(12) United States Patent
Lepore et al.

(10) Patent No.: US 10,759,735 B2
(45) Date of Patent: Sep. 1, 2020

(54) BRIDGED BICYCLIC COMPOUNDS AND THEIR DERIVATIVES AS NEUROPROTECTIVE AGENTS AND METHODS OF USE THEREOF

(71) Applicant: Florida Atlantic University Board of Trustees, Boca Raton, FL (US)

(72) Inventors: Salvatore D. Lepore, Delray Beach, FL (US); Kenneth Dawson-Scully, Boca Raton, FL (US); Elijah J. St. Germain, Davie, FL (US); Samantha L. Maki, Delray Beach, FL (US); Wesley L. Bollinger, Dallas, TX (US); Nadia K. Sial, Boca Raton, FL (US)

(73) Assignee: Florida Atlantic University Board of Trustees, Boca Raton, FL (US)

(*) Notice: Subject to any disclaimer, the term of this patent is extended or adjusted under 35 U.S.C. 154(b) by 0 days.

(21) Appl. No.: 16/245,587

(22) Filed: Jan. 11, 2019

(65) Prior Publication Data

US 2019/0284123 A1    Sep. 19, 2019

Related U.S. Application Data

(60) Provisional application No. 62/642,627, filed on Mar. 14, 2018.

(51) Int. Cl.
| | |
|---|---|
| *A61K 31/192* | (2006.01) |
| *A61K 31/191* | (2006.01) |
| *C07C 69/753* | (2006.01) |
| *C07C 67/03* | (2006.01) |
| *A61P 25/00* | (2006.01) |
| *A61P 25/06* | (2006.01) |
| *A61P 25/28* | (2006.01) |
| *A61P 9/04* | (2006.01) |
| *C07C 62/34* | (2006.01) |
| *C07C 69/18* | (2006.01) |

(52) U.S. Cl.
CPC .......... *C07C 69/753* (2013.01); *A61P 25/00* (2018.01); *C07C 62/34* (2013.01); *C07C 67/03* (2013.01); *C07C 69/18* (2013.01); *C07C 2602/44* (2017.05); *C07C 2602/46* (2017.05)

(58) Field of Classification Search
CPC .. A61K 31/192; A61K 31/191; C07C 69/753; C07C 67/03; A61P 25/00; A61P 25/06; A61P 25/28; A61P 9/04
USPC ...................... 514/544, 546, 543; 560/73, 67
See application file for complete search history.

(56) References Cited

PUBLICATIONS

Maity, P. and S. Lepore, "Anion-catalyzed addition of v-silylallenyl esters to aldehydes: A new entry into [3.2.1] bicyclic natural products", J. Am. Chem. Soc. 2009, 131, pp. 4196-4197. (Year: 2009).*

* cited by examiner

*Primary Examiner* — Matthew P Coughlin
*Assistant Examiner* — Sagar Patel
(74) *Attorney, Agent, or Firm* — Fox Rothschild LLP

(57) ABSTRACT

Neuroprotective compounds for reducing neurological damage due to cellular stress in an individual are of Formula 1:

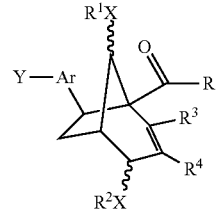

or an enantiomer, diastereomer, racemic mixture or a pharmaceutically acceptable salt thereof, wherein: Ar=aryl; Y=aryl substituent (ortho, meta, or para) selected from the group consisting of: alkyl, alkyloxy, alkylamino, $R^5R^6N$, and halo; X=O, N, or S; R=H, alkyl, aryl, OH, alkyloxy, aryloxy, $NH_2$, alkylamino, $R^5R^6N$, or arylamino; $R^1$ and $R^2$=alkylcarbonyl, arylcarbonyl, alkyl, or H, individually; $R^3$=arylCH=CH, alkylCH=CH, alkyl; $R^4$=H, alkyl, or aryl; and $R^5$ and $R^6$=alkyl, individually. Methods of reducing neurological damage due to cellular stress in an individual include administering to the individual during or after the cellular stress a neuroprotective compound of Formula I in a therapeutically effective amount to restore synaptic function during or after the cellular stress.

19 Claims, 8 Drawing Sheets

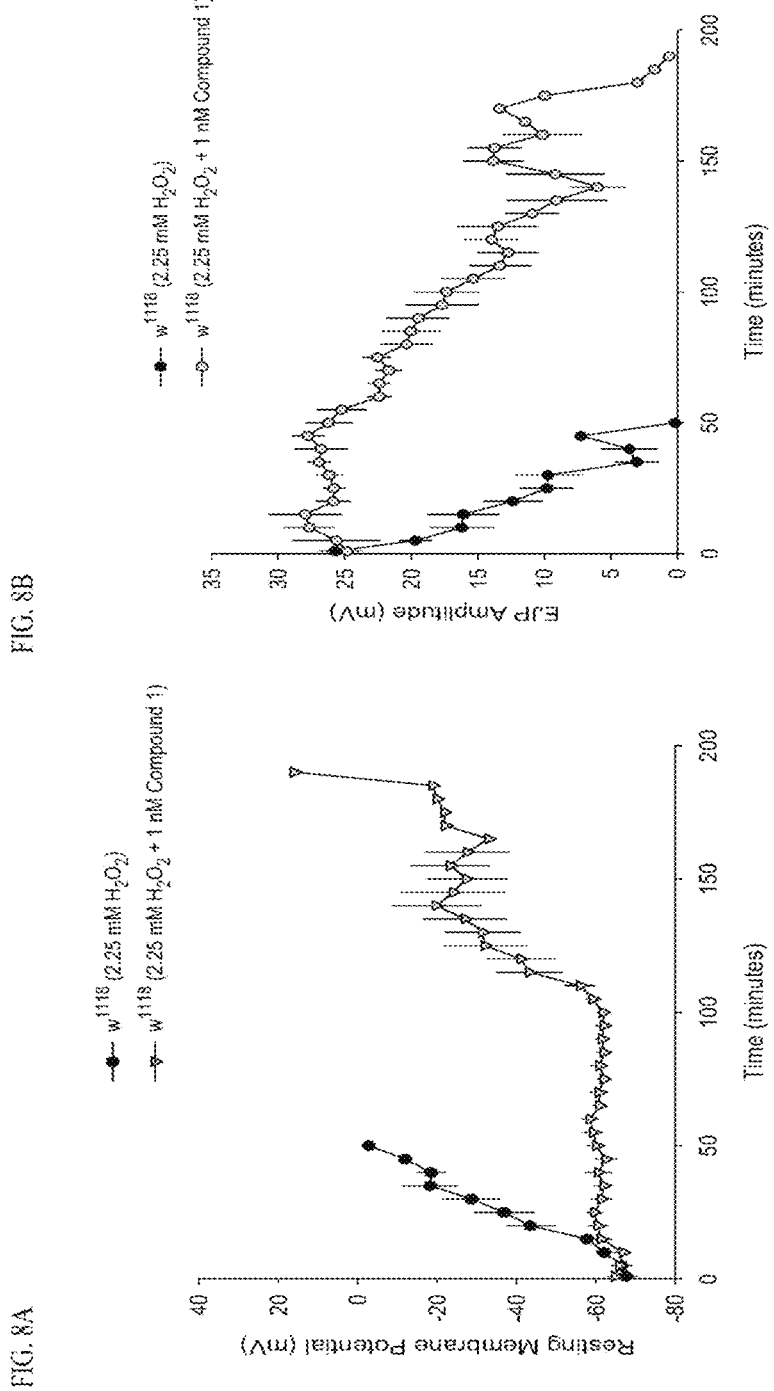

BRIDGED BICYCLIC COMPOUNDS AND THEIR DERIVATIVES AS NEUROPROTECTIVE AGENTS AND METHODS OF USE THEREOF

CROSS-REFERENCE TO RELATED APPLICATION

This application claims priority to U.S. Provisional Application No. 62/642,627 filed Mar. 14, 2018, which is herein incorporated by reference in its entirety.

STATEMENT REGARDING FEDERALLY SPONSORED RESEARCH

This invention was made with government support under grant no. 2R15GM110651-02 awarded by the National Institutes of Health (NIH) (NIGMS). The government has certain rights in the invention.

FIELD OF THE INVENTION

The invention relates generally to the fields of pharmacology, medicine, and neurology. In particular, the invention relates to novel compounds possessing unique molecular features and exhibiting neuroprotective effects.

BACKGROUND

An example of a small molecule neuroprotectant that has found medical use and entered the market is the drug edaravone, which is used in the treatment of stroke and amyotrophic lateral sclerosis. Although this compound is considered a free radical scavenger due to its ability to donate an electron, it may have other mechanisms of biochemical action as well. Small molecules that induce acute neuroprotection are rare. For example, a glial cell derived neurotrophic factor (GDNF) upregulating small molecule (named GSK812) that prevents retinal degradation has not been shown to be effective across a number of cell types. No neuroprotective Food and Drug Administration (FDA)-approved drugs exist that effectively reduce neurological damage elicited by acute oxidative stress. Drugs capable of restoring synaptic function during or after oxidative stress are urgently needed.

SUMMARY

Described herein are novel much needed neuroprotective compounds capable of restoring synaptic function during or after oxidative stress in an individual. Compounds containing a mostly-saturated all-carbon bridged bicyclic scaffold, such as those described herein, are relatively rare in drug design. The novel features of this compound class include a highly 'three-dimensional' core scaffold and the presence of five contiguous chiral centers. General trends have been observed between the physical properties of small molecules and clinical efficacy as drug candidates. One such trend is between 'architectural complexity' and biological activity. While architectural molecular complexity can be measured in different ways, the degree of saturation and number of chiral centers are two important components (Lovering et al. J. Med. Chem. 2009, 52, 6752-6756). The $Fsp^3$ value has been used to quantify molecular complexity; it is defined as the ratio of the number of saturated carbons in a molecule to the entire number of carbons present in a given molecule. The greater $Fsp^3$ of the example bridged bicyclic compound (see FIG. 1) versus resveratrol is indicative of the greater degree of three-dimensionality and asymmetry of the former compared to the planar resveratrol. By their very nature, $sp^3$ centers allow for molecular appendages to exist in nonplanar arrangements relative to each other. Increased $sp^3$ centers should lead to more finely tuned complementarity between a designed molecule and the active site of a biological target and thus to greater selectivity. Based on these considerations, the [3.2.1] bicyclic motif of the neuroprotective compounds described herein is an ideal scaffold in the design of bioactive compounds (FIG. 1). This bicyclic scaffold confers increased saturation and chiral centers without adding rotatable bonds; conventional wisdom is that medicinal compounds should have less than ten rotatable bonds (Veber et al. J. Med. Chem. 2002, 45, 2615-2623).

Accordingly, described herein is a compound of Formula 1:

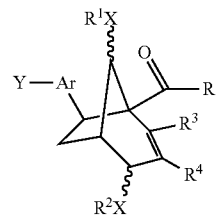

or an enantiomer, diastereomer, racemic mixture or a pharmaceutically acceptable salt or solvate thereof, wherein:

Ar=aryl;

Y=aryl substituent (ortho, meta, or para) selected from the group consisting of: alkyl, alkyloxy, alkylamino, $R^5R^6N$, and halo;

X=O, N, or S;

R=H, alkyl, aryl, OH, alkyloxy, aryloxy, $NH_2$, alkylamino, $R^5R^6N$, or arylamino;

$R^1$ and $R^2$=alkylcarbonyl, arylcarbonyl, alkyl, or H, individually;

$R^3$=arylCH=CH, alkylCH=CH, alkyl;

$R^4$=H, alkyl, or aryl; and $R^5$ and $R^6$=alkyl, individually.

In some embodiments of the compound, alkyl is a saturated hydrocarbon moiety containing up to six carbons; and, aryl is a 5- or 6-membered aryl or heteroaryl group. In some embodiments, the alkyl is an alkyloxy, alkylamino, alkylCH=CH, or alkylcarbonyl. In one embodiment, the compound has the formula:

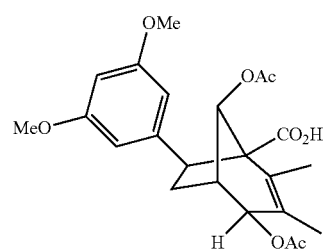 [SMILES: COc1cc(OC)cc(C2CC3C(OC(C)=O)C(C)=C(C)C2(C(=O)O)C3OC(C)=O)c1]

or an enantiomer, diastereomer, racemic mixture or a pharmaceutically acceptable salt thereof. In another embodiment, the compound has the formula:

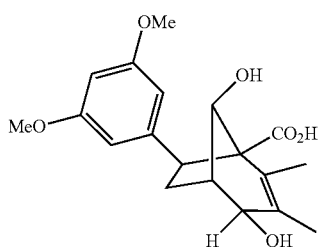 [SMILES: COc1cc(OC)cc(C2CC3C(O)C(C)=C(C)C2(C(=O)O)C3O)c1]

or an enantiomer, diastereomer, racemic mixture or a pharmaceutically acceptable salt thereof. In another embodiment, the compound has the formula:

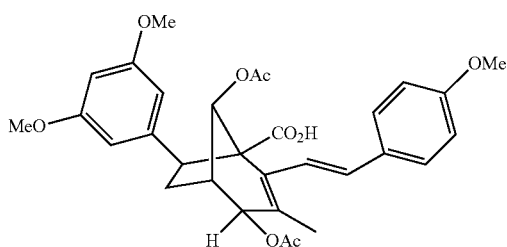 [SMILES: COc1ccc(/C=C/C2=C(C)C(OC(C)=O)C3CC(c4cc(OC)cc(OC)c4)C2(C(=O)O)C3OC(C)=O)cc1]

or an enantiomer, diastereomer, racemic mixture or a pharmaceutically acceptable salt thereof. In another embodiment, the compound has the formula:

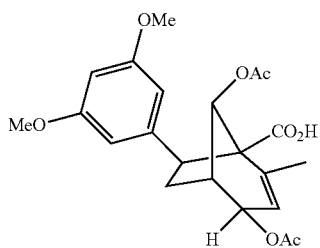 [SMILES: COc1cc(OC)cc(C2CC3C(OC(C)=O)C=C(C)C2(C(=O)O)C3OC(C)=O)c1]

or an enantiomer, diastereomer, racemic mixture or a pharmaceutically acceptable salt thereof. In another embodiment, the compound has the formula:

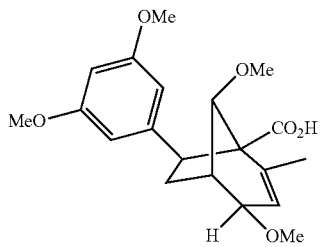 [SMILES: COc1cc(OC)cc(C2CC3C(OC)C=C(C)C2(C(=O)O)C3OC)c1]

or an enantiomer, diastereomer, racemic mixture or a pharmaceutically acceptable salt thereof.

Also described herein is a composition including any of the compounds of Formula I above, and a pharmaceutically acceptable carrier. In one embodiment of a composition, the compound has the formula:

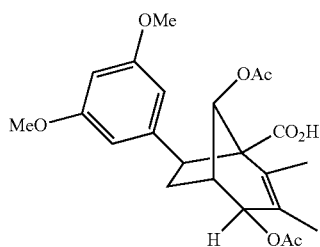 [SMILES: COc1cc(OC)cc(C2CC3C(OC(C)=O)C(C)=C(C)C2(C(=O)O)C3OC(C)=O)c1]

or an enantiomer, diastereomer, racemic mixture or a pharmaceutically acceptable salt thereof. In another embodiment of a composition, the compound has the formula:

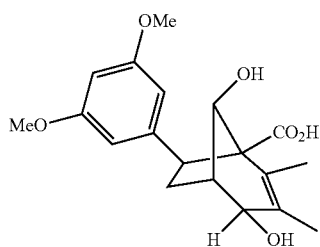 [SMILES: COc1cc(OC)cc(C2CC3C(O)C(C)=C(C)C2(C(=O)O)C3O)c1]

or an enantiomer, diastereomer, racemic mixture or a pharmaceutically acceptable salt thereof. In another embodiment of a composition, the compound has the formula:

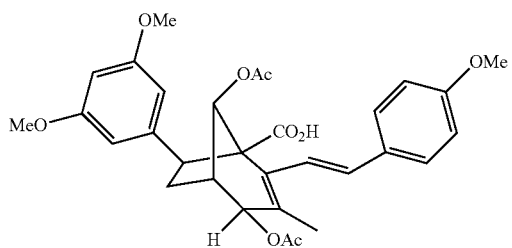 [SMILES: COc1ccc(/C=C/C2=C(C)C(OC(C)=O)C3CC(c4cc(OC)cc(OC)c4)C2(C(=O)O)C3OC(C)=O)cc1]

or an enantiomer, diastereomer, racemic mixture or a pharmaceutically acceptable salt thereof. In another embodiment of a composition, the compound has the formula:

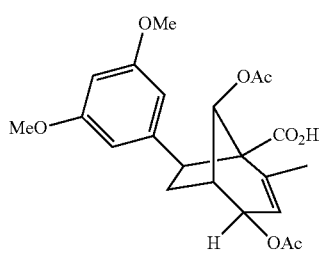 [SMILES: COc1cc(OC)cc(C2CC3C(OC(C)=O)C=C(C)C2(C(=O)O)C3OC(C)=O)c1]

or an enantiomer, diastereomer, racemic mixture or a pharmaceutically acceptable salt thereof. In another embodiment of a composition, the compound has the formula:

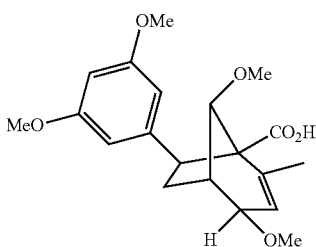 [SMILES: COc1cc(OC)cc(C2CC3C(OC)C=C(C)C2(C(=O)O)C3OC)c1]

or an enantiomer, diastereomer, racemic mixture or a pharmaceutically acceptable salt thereof.

Further described herein is a method of reducing neurological damage due to cellular stress in an individual (e.g., a human). The method includes administering to the individual during or after the cellular stress any of the compounds or compositions above in a therapeutically effective amount to restore synaptic function during or after the cellular stress, the cellular stress being anoxia or oxidative stress. In some embodiments, the cellular stress is acute oxidative stress. The cellular stress can be caused by, for example, one more of migraine, Alzheimer's disease, traumatic brain injury, heart attack and stroke. Typically, administering the compound or composition to the individual increases time until synaptic failure. The method can further include detecting a state or condition of cellular stress in the individual prior to administering to the individual during or after the cellular stress any of the compounds or compositions described above.

The terms "group," "functional group," "pendant group," "moiety," "molecular moiety," or the like are somewhat synonymous in the chemical arts and are used to refer to distinct, definable portions or units of a molecule, and to units that perform some function. Examples of functional groups that are suitable for the compounds described herein include, but are not limited to, aryl or heteroaryl group, alkyoxy, alkylamino, alkylthio, dialkylamino, halo, hydroxy, amino, thiol, arylamino, alkanoyl, arylcarbonyl, arylvinyl, alkylvinyl, or the like.

As used herein, the term "aryl" refers to aromatic hydrocarbons such as phenyl and naphthyl that may be substituted with a variety of functional and/or alkyl groups (e.g., C1-C6 alkyl).

As used herein, the term "heteroaryl" refers to aromatic cycles where one or more heteroatoms form part of the ring. The heteroaryl ring may also be substituted with a variety of functional and/or alkyl groups (e.g., C1-C6 alkyl).

As used herein, the term "alkyl" refers to a saturated hydrocarbon fragment. For example, in one embodiment, an alkyl can be a saturated hydrocarbon moiety containing up to six carbons (e.g., methyl, ethyl).

As used herein, the term "alkyoxy" refers to a group comprised of an alkyl group connected to an oxygen (e.g., methoxy, ethyoxy)

As used herein, the term "alkylamino" refers to a group comprised of an alkyl group connected to a trivalent nitrogen (e.g., methylamino, ethylamino).

As used herein, the term "dialkylamino" refers to a group comprised of two alkyl groups (though not necessarily the same) connected to a trivalent nitrogen (e.g., dimethylamino, diethylamino, ethylmethylamino).

As used herein, the term "arylamino" refers to an aryl group connected to a trivalent nitrogen.

As used herein, the term "alkanoyl" refers an alkyl group connected to a carbonyl.

As used herein, the term "arylcarbonyl" refers an aryl group connected to a carbonyl.

As used herein, the term "arylvinyl" refers to an aryl group connected to an ethylene group (e.g., phenylvinyl, also abbreviated as $C_6H_5CHCH$).

As used herein, the term "alkylvinyl" refers to an alkyl group connected to an ethylene group (e.g., methylvinyl, also abbreviated as $CH_3CHCH$).

As used herein, the term "halo" or "halogen" refers to F, Cl, Br, or I.

As used herein, when referring to a compound, the terms "biologically active compound" and "bioactive compound" mean a compound having a physiological or biological effect on animals or humans or cells therefrom.

By the term "neuroprotective compound" is meant any compound that is capable of restoring synaptic function during or after cellular stress in an individual. In some embodiments, a neuroprotective compound is a compound of Formula 1:

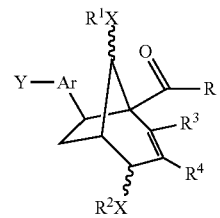

or a pharmaceutically acceptable salt or solvate thereof, wherein: Ar=aryl; Y=aryl substituent (ortho, meta, or para) selected from the group consisting of: alkyl, alkyloxy, alkylamino, $R^5R^6N$, and halo; X=O, N, or S; R=H, alkyl, aryl, OH, alkyloxy, aryloxy, $NH_2$, alkylamino, $R^5R^6N$, or arylamino; $R^1$ and $R^2$=alkylcarbonyl, arylcarbonyl, alkyl, or H, individually ($R^1$ and $R^2$ can be the same group, or they can be different groups); $R^3$=arylCH=CH, alkylCH=CH, alkyl; $R^4$=H, alkyl, or aryl; and $R^5$ and $R^6$=alkyl, individually ($R^5$ and $R^6$ can be the same group, or they can be different groups).

As depicted in FIG. 3, the term "resveramorph" refers to a scaffold where the planar structure of resveratrol is morphed (modified) into one containing a significant amount of three-dimensional character, specifically, a bridged bicycle. As described in the Examples below, some resveramorphs, such as compound 1, exhibit neuroprotective properties.

The term "purified" means separated from many other entities (small molecules, compounds, proteins, nucleic acids), and does not require the material to be present in a form exhibiting absolute purity, exclusive of the presence of other entities. In some embodiments, a small molecule, compound, protein, nucleic acid or other entity is considered pure (purified) when it is removed from substantially all other entities.

By the terms "to modulate" and "modulates" is meant to increase or decrease. These terms can refer to increasing or decreasing an activity, level or function of a molecule (e.g., protein, peptide, nucleic acid, small molecule, metabolite), or effecting a change with respect to one or more biological or physiological mechanisms, effects, responses, functions, pathways or activities in which, for example, cellular stress (e.g., anoxia, oxidative stress) is involved.

The terms "agent" and "therapeutic agent" as used herein refer to a chemical entity or biological product, or combination of chemical entities or biological products, administered to a subject (a mammal such as a human) to treat a disease or condition (e.g., a neurological condition, neurological damage, etc.). Examples of therapeutic agents include small molecules (compounds) and biologics, which may be referred to herein as a "drug" or "therapeutic drug".

The terms "patient," "subject" and "individual" are used interchangeably herein, and mean a subject, typically a mammal, to be treated, diagnosed, and/or to obtain a biological sample from. Subjects include, but are not limited to, humans, non-human primates, horses, cows, sheep, pigs, rats, mice, insects, dogs, and cats. A human in need of neurological damage treatment is an example of a subject.

The terms "sample," "patient sample," "biological sample," and the like, encompass a variety of sample types obtained from a patient, individual, or subject and can be used in a therapeutic drug screening, diagnostic or monitoring assay. The patient sample may be obtained from a healthy subject, a diseased patient or a patient having associated symptoms of a particular disease or disorder (e.g., a neurological disorder). Moreover, a sample obtained from a patient can be divided and only a portion may be used for therapeutic drug screening. Further, the sample, or a portion thereof, can be stored under conditions to maintain sample for later analysis. The definition specifically encompasses blood and other liquid samples of biological origin (including, e.g., cerebrospinal fluid, plasma, serum, peripheral blood), solid tissue samples such as a biopsy specimen or tissue cultures or cells derived therefrom and the progeny thereof. In a specific embodiment, a sample includes a cerebrospinal fluid sample. In another embodiment, a serum sample is used. The definition also includes samples that have been manipulated in any way after their procurement, such as by centrifugation, filtration, precipitation, dialysis, chromatography, treatment with reagents, washing, or enriched for certain cell populations. The terms further encompass a clinical sample, and also include cells in culture, cell supernatants, tissue samples, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

As used herein, the terms "therapeutic treatment" and "therapy" are defined as the application or administration of a therapeutic agent (e.g., a neuroprotective compound as described herein) or therapeutic agents to a patient who has a disease, a symptom of disease or a predisposition toward a disease, with the purpose to cure, heal, alleviate, relieve, alter, remedy, ameliorate, improve or affect the disease, the symptoms of disease, or the predisposition toward disease.

Although compounds, compositions, methods and kits similar or equivalent to those described herein can be used in the practice or testing of the present invention, suitable compounds, compositions, methods and kits are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIGS. 8A and 8B are a pair of graphs showing that during acute oxidative stress, *Drosophila* larval muscle resting membrane potential (RMP) and EJP amplitude decline. 8A) RMP from larval muscle 6 was observed to steadily depolarize in $w^{1118}$ larvae exposed to 2.25 mM $H_2O_2$ alone and 2.25 mM $H_2O_2$ with 1 nM compound 1 (n=5 per group). 8B) EJP amplitude was recorded in the same larval preparations (n=5 per group). Loss of RMP was found to track EJP amplitude decline across treatments. Data is presented as mean±SEM.

DETAILED DESCRIPTION

Figure 1:
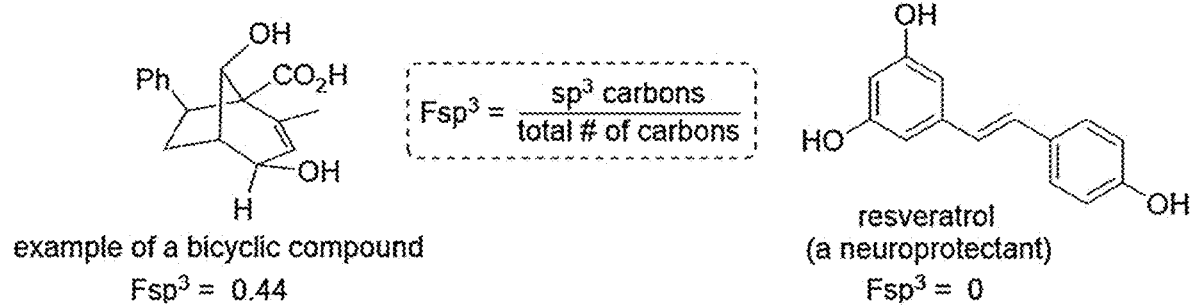
FIG. 1 shows measures of architectural complexity of some embodiments of molecular structures (compounds) as described herein.

Described herein are novel neuroprotective compounds, methods of preparing and synthesizing these compounds, and the use of these compounds for reducing, treating or preventing neurological damage caused by oxidative stress. In the Examples below, the novel neuroprotective compounds produced dose-dependent protection of neurotransmission from acute oxidative stress.

Neuroprotective Compounds and Compositions Thereof

In one embodiment, a neuroprotective compound is of Formula 1:

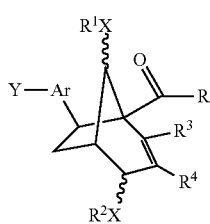

or a pharmaceutically acceptable salt or solvate thereof, wherein:

Ar=aryl;

Y=aryl substituent (ortho, meta, or para), e.g., alkyl, alkyloxy, alkylamino, $R^5R^6N$, and halo;

X=O, N, or S;

R=H, alkyl, aryl, OH, alkyloxy, aryloxy, $NH_2$, alkylamino, $R^5R^6N$, or arylamino;

$R^1$ and $R^2$=alkylcarbonyl, arylcarbonyl, alkyl, or H, individually;

$R^3$=arylCH=CH, alkylCH=CH, alkyl;

$R^4$=H, alkyl, or aryl; and $R^5$ and $R^6$=alkyl, individually.

The compounds described herein may exist as different diastereomeric isomers than those exemplified both as racemates as well as non-racemic or enantiopure forms.

In one embodiment of a neuroprotective compound according to Formula 1, an alkyl is a saturated hydrocarbon moiety containing up to six carbons, and an aryl is a 5- or 6-membered aryl or heteroaryl group. Any suitable alkyl can be used. Examples of alkyl-containing substituents that can be used in the neuroprotective compounds described herein include alkyloxy, alkylamino, alkylCH=CH, and alkylcarbonyl. Similarly, any suitable aryl can be used. Examples of aryl-containing substituents that can be used in the compounds described herein include arylcarbonyl, arylamino, and arylvinyl. When referring to an aryl substituent, it may be, for example, one that is ortho, meta and/or para substituted.

In one embodiment of a neuroprotective compound according to Formula 1, the compound has the formula (and its enantiomer):

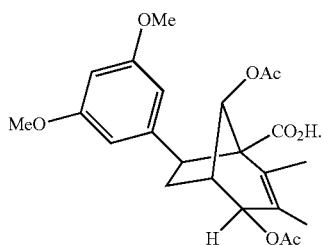 [SMILES: COc1cc(OC)cc(C2CC3C(OC(C)=O)C(C)=C(C)C2(C(=O)O)C3OC(C)=O)c1]

In another embodiment of a neuroprotective compound according to Formula 1, the compound has the formula (and its enantiomer):

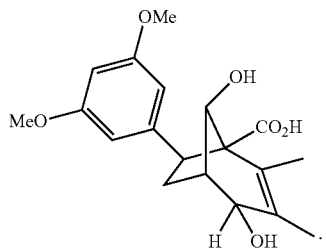

In another embodiment of a neuroprotective compound according to Formula 1, the compound has the formula (and its enantiomer):

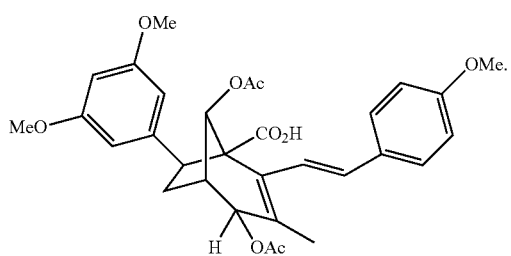 [SMILES: COc1ccc(/C=C/C2=C(C)C(OC(C)=O)C3CC(c4cc(OC)cc(OC)c4)C2(C(=O)O)C3OC(C)=O)cc1]

In another embodiment of a neuroprotective compound according to Formula 1, the compound has the formula (and its enantiomer):

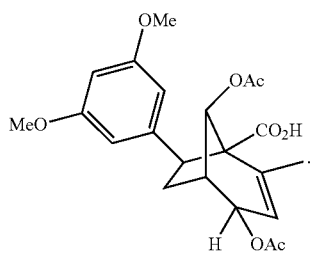

In another embodiment of a neuroprotective compound according to Formula 1, the compound has the formula (and its enantiomer):

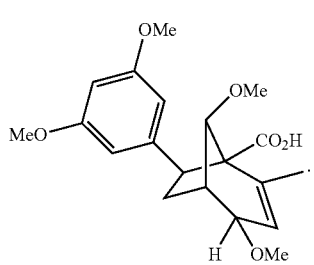

In some embodiments, a neuroprotective compound as described herein encompasses any other combinations of the structural features described herein.

Compositions including a neuroprotective compound according to any embodiments described herein typically also include a pharmaceutically acceptable carrier. Methods of making the neuroprotective compounds are described in detail in the Examples below.

Methods of Treating, Reducing and Preventing Neurological Damage

Methods of reducing neurological damage due to cellular stress in an individual include administering to the individual, during or after the cellular stress, a neuroprotective compound as described herein or a composition including a neuroprotective compound as described herein in a therapeutically effective amount to restore synaptic function during or after the cellular stress. In some embodiments, the individual is suffering from or subjected to anoxia or oxidative stress. The neuroprotective compounds and compositions described herein may be used to treat, reduce or prevent any type of neurological damage caused by cellular stress (e.g., oxidative stress, acute oxidative stress, anoxia). Specific examples of neurological damage caused by cellular stress include behavioral dysfunction, neurological impairment, visual or auditory impairment, synaptic failure, decreased time to synaptic failure, impaired synaptic function, impaired transmission, and neuronal damage or death. For example, administering the neuroprotective compound or composition to the individual increases time until synaptic failure. Cellular stress, e.g., oxidative stress and anemia, can be cellular stress resulting from any pathology. Examples of pathologies that cause cellular stress include migraine, Alzheimer's disease, traumatic brain injury, heart attack and stroke. A dosage amount for an individual may be based on achieving concentrations at the cell required for neuroprotection (e.g. 0.5 nM).

The methods described herein can further include detecting a state or condition of cellular stress in the individual. The detection is typically done prior to administering to the individual during or after the cellular stress a neuroprotective compound or a composition including a neuroprotective compound. Methods of detecting cellular stress in an individual are well known in the art, and include detection of behavioral dysfunction, seizures, neurological deficits including visual or auditory impairment, etc.

Any suitable methods of administering a neuroprotective compound or composition as described herein to an individual may be used. In these methods, the compounds and compositions can be administered to an individual by any suitable route, e.g., oral, buccal (e.g., sub-lingual), parenteral (e.g., subcutaneous, intramuscular, intradermal, or intravenous), and topical (i.e., both skin and mucosal surfaces, including airway surfaces), administration. In an embodiment, a neuroprotective compound or composition may be administered systemically by intravenous injection. In another embodiment, a neuroprotective compound or composition may be administered directly to a target site, by, for example, surgical delivery to an internal or external target site, or by catheter to a site accessible by a blood vessel. If administered via intravenous injection, the compound or composition may be administered in a single bolus, multiple injections, or by continuous infusion (e.g., intravenously, by peritoneal dialysis, pump infusion). For parenteral administration, the compound or composition is preferably formulated in a sterilized pyrogen-free form.

As indicated above, a neuroprotective compound or composition as described herein may be in a form suitable for sterile injection. To prepare such a composition, the suitable active therapeutic agent(s) (e.g., a therapeutically effective amount of a neuroprotective compound) is dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution (D5W, 0.9% sterile saline). The aqueous formulation may also contain one or more preservatives (e.g., methyl, ethyl or n-propyl p-hydroxybenzoate). In cases where the therapeutic agent(s) (1 or more neuroprotective compounds) is only sparingly or slightly soluble in water, a dissolution enhancing or solubilizing agent can be added, or the solvent may include 10-60% w/w of propylene glycol or the like. The compounds and compositions described herein may be administered to an individual (e.g., rodents, humans, nonhuman primates, canines, felines, ovines, bovines, insects) in any suitable formulation according to conventional pharmaceutical practice (see, e.g., *Remington: The Science and Practice of Pharmacy* (21st ed.), ed. A. R. Gennaro, Lippincott Williams & Wilkins, (2005) and *Encyclopedia of Pharmaceutical Technology*, ($3^{rd}$ ed.) eds. J. Swarbrick and J. C. Boylan, Marcel Dekker, CRC Press, New York (2006), a standard text in this field, and in USP/NF). A description of exemplary pharmaceutically acceptable carriers and diluents, as well as pharmaceutical formulations, can be found in Remington: supra. Other substances may be added to the compounds and compositions to stabilize and/or preserve them.

The therapeutic methods described herein in general include administration of a therapeutically effective amount of the neuroprotective compounds and compositions described herein to an individual (e.g., human) in need thereof, particularly a human. Such treatment will be suitably administered to individuals, particularly humans, suffering from, having, susceptible to, or at risk for a disease, disorder, or symptom thereof (e.g., cellular stress, neurological damage). Determination of those individuals "at risk" can be made by any objective or subjective determination by a diagnostic test or opinion of a subject or health care provider.

Methods of Measuring Neuroprotective Effects

Small molecule-mediated neuroprotection is an area of research that has important implications for several maladies such as migraine, Alzheimer's disease, and stroke. One promising method to measure the neuroprotective effects of various medicinal compounds against oxidative stress in *D. melanogaster* has been developed (Caplan et al. Journal of Neurophysiology, 2013, 109, 3, 649-658). In this phenotypic model, fly larvae have their synaptic transmission measured via electrical probes in the post-synaptic neuromuscular junction (NMJ). The time until synaptic failure is first measured to obtain a control. An oxidizing solution (2.25 mM of hydrogen peroxide) is then introduced to the tissue and the time to synaptic failure is again measured. Hydrogen peroxide greatly reduces the time to synaptic failure relative to the control by damaging neurons through oxidative stress. Once the time to synaptic failure has been established with hydrogen peroxide alone, then different compounds can be introduced at varying concentrations along with the hydrogen peroxide solution, and their effects on the time to synaptic failure are measured and compared to the two controls.

In the neuroprotective compounds and methods described herein, any suitable protocol and/or model can be used to measure the neuroprotective effects of a compound.

Effective Doses

The neuroprotective compounds and compositions described herein are preferably administered to an individual in need thereof (e.g., human having neurological damage, and/or subjected to cellular stress) in an effective amount, that is, an amount capable of producing a desirable result in a treated individual. Desirable results include one or more of, for example, decreasing or preventing synaptic failure, increasing time to synaptic failure, restoring impaired synaptic function, decreasing or preventing neuronal death or damage, and prolonging survival. Such a therapeutically effective amount can be determined according to standard methods. Toxicity and therapeutic efficacy of the neuroprotective compounds and compositions utilized in the methods described herein can be determined by standard pharmaceutical procedures. As is well known in the medical and veterinary arts, dosage for any one individual depends on many factors, including the individual's size, body surface area, age, the particular composition to be administered, time and route of administration, general health, and other drugs being administered concurrently. A delivery dose of a neuroprotective composition as described herein is determined based on preclinical efficacy and safety.

Kits

Described herein are kits for reducing neurological damage due to cellular stress in an individual. A typical kit includes a composition including a neuroprotective compound as described herein and a pharmaceutically acceptable carrier, and instructions for use. Kits also typically include a container and packaging. Instructional materials for preparation and use of the kit components are generally included. While the instructional materials typically include written or printed materials, they are not limited to such. Any medium capable of storing such instructions and communicating them to an end user is encompassed by the kits herein. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The present invention is further illustrated by the following specific examples. The examples are provided for illustration only and should not be construed as limiting the scope of the invention in any way.

Example 1

Synthesis and Testing of Neuroprotective Compounds

The synthesis of an all-carbon [3.2.1]bicycle proceeds through an α,α'-addition strategy adapting approaches previously described (Bhat et al., J. Org. Chem. 2014, 79, 9402; Maity et al. J. Am. Chem. Soc. 2009, 131, 4196). The first stage is the construction of the 5-carbon cyclic ketoester with the appropriate pendant group(s) on the ring carbons that will become the 2-carbon bridge of the bicyclic target. An aryl moiety and ester are installed on commercially available and inexpensive cyclopent-2-enone via a cuprate addition followed by trapping with ethyl cyanoformate to furnish ketoester intermediate 1 (Scheme 1). The ester is transesterified to afford intermediate 2 bearing a protecting group that is removed under mild fluoride treatment later in the synthesis. Synthesis of the required lactone intermediates is then accomplished using cesium carbonate or potassium tert-butoxide. The addition to the β-carbon of allenoate intermediates 3 or 4 leads to lactone intermediates 5 or 6 (Scheme 2).

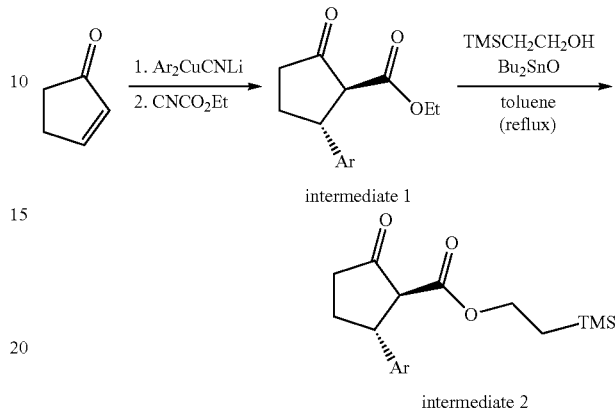

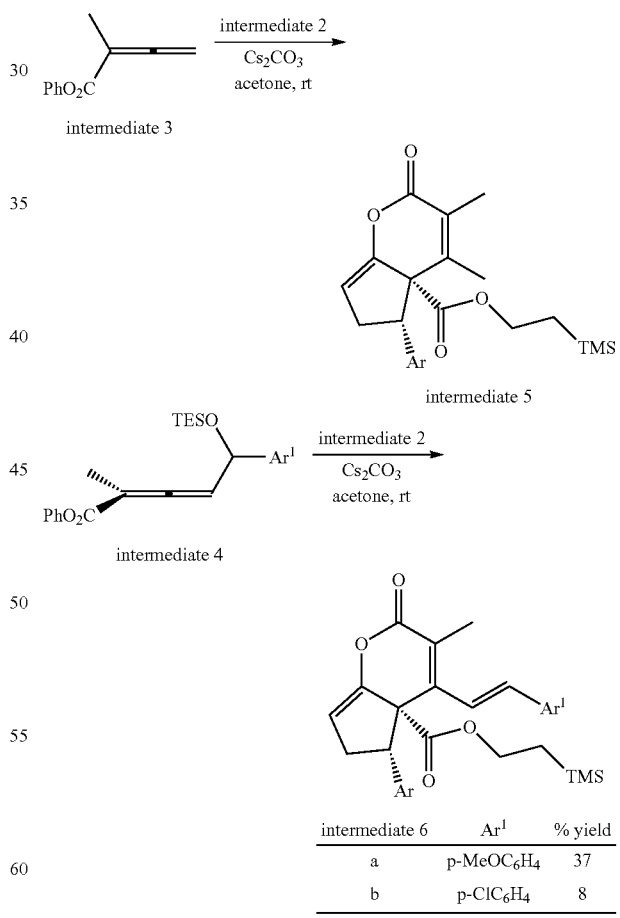

The construction of the C5-C4 bond leads to a bridged bicycle. This bond is formed with control of the configuration of the C5 carbon since only syn addition of the 3-carbon bridge is possible (Scheme 3). However, this bond-forming step also occurs with control of configuration of the C4 carbon via a "reductive aldol" mechanism likely involving an aluminum chelated six-membered ring transition state.

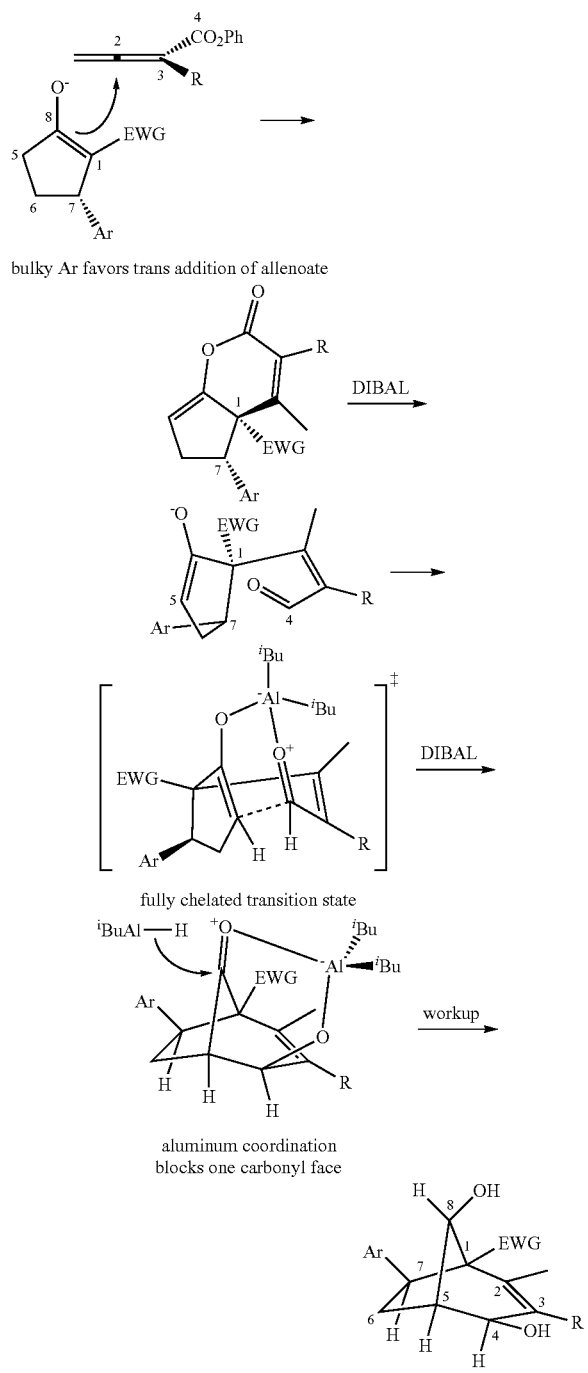

Scheme 3. Diastereoselective mechanism of addition/annulation of allenoates to aryl-substituted cyclopentanes.

In the synthesis methods described herein, the reductive aldol of lactones such as intermediates 5 and 6 leads to compounds bridged bicyclic diols such as intermediate 7 as primarily single diastereomers. As mentioned above, the preference for the observed relative stereochemistry can be explained by invoking a cyclic transition state model (Scheme 3), which have been proposed in similar intramolecular systems. In the proposed transition state, the in-situ formed α,β-unsaturated aldehyde is chelated to aluminum along with the enolate oxygen such that the former is in the s-trans configuration and an approximation of the 6-membered Zimmerman-Traxler chair conformation is achieved. This transition state leads to facial selectivity of the enolate attack on the aldehyde carbonyl. This results in an exo configuration of the hydroxyl on the C4 (on the 3-carbon bridge). This mechanism also provides a rationale for the observed preference for reduction of the carbonyl on C8 (on the 1-carbon bridge) on the face leading to the endo hydroxyl, as the other face would be less sterically accessible due to aluminum complexation from the first reduction.

Upon synthesis of bridged bicyclic compounds such as intermediates 7 and 10, the hydroxyls were acetyl protected in nearly quantitative yields using a standard procedure to afford intermediates 8 and 11. The compounds were then treated with TBAF in THF at room temperature, the silyl ester was cleanly removed to reveal compounds 1 and 3 in acceptable yields.

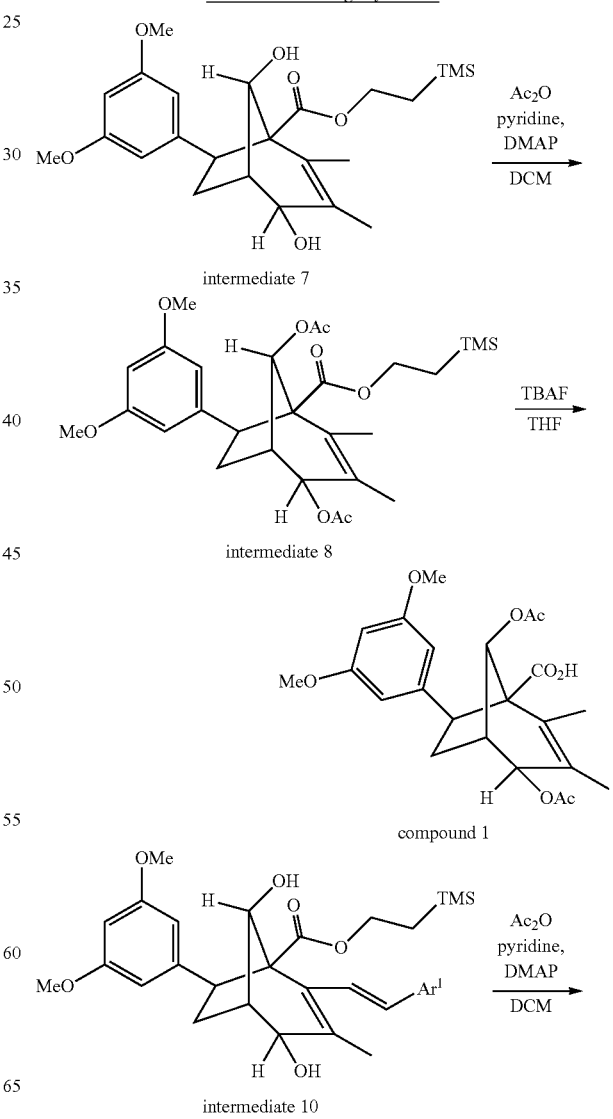

Scheme 4. End stage synthesis.

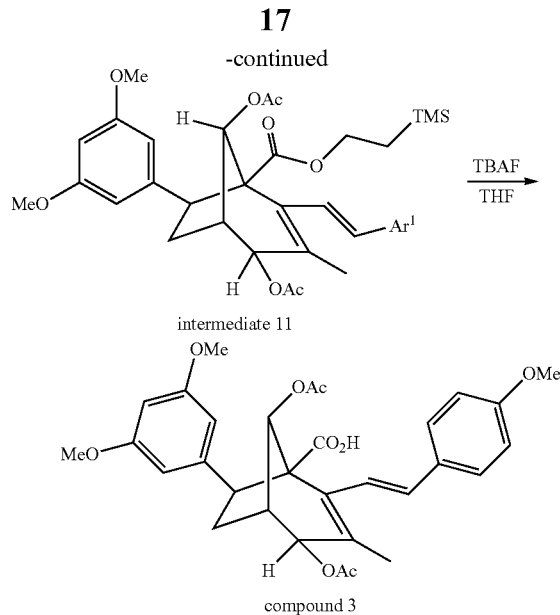

intermediate 11 compound 3

Figure 2:
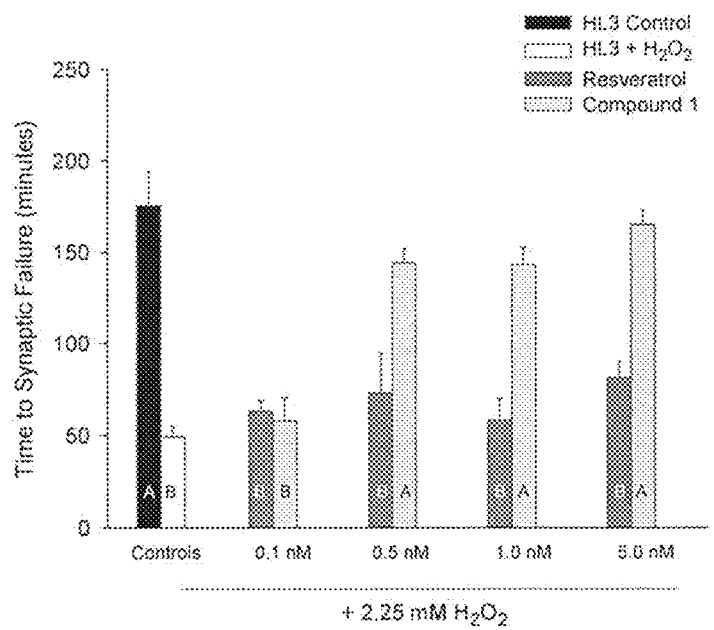
FIG. 2 shows results from screening of compound 1 (top (bar graph)) and the structure of some neuroprotective compounds (bottom) as described herein evaluated for neuroprotection against oxidative stress in *Drosophila melanogaster*.
Figure 2:
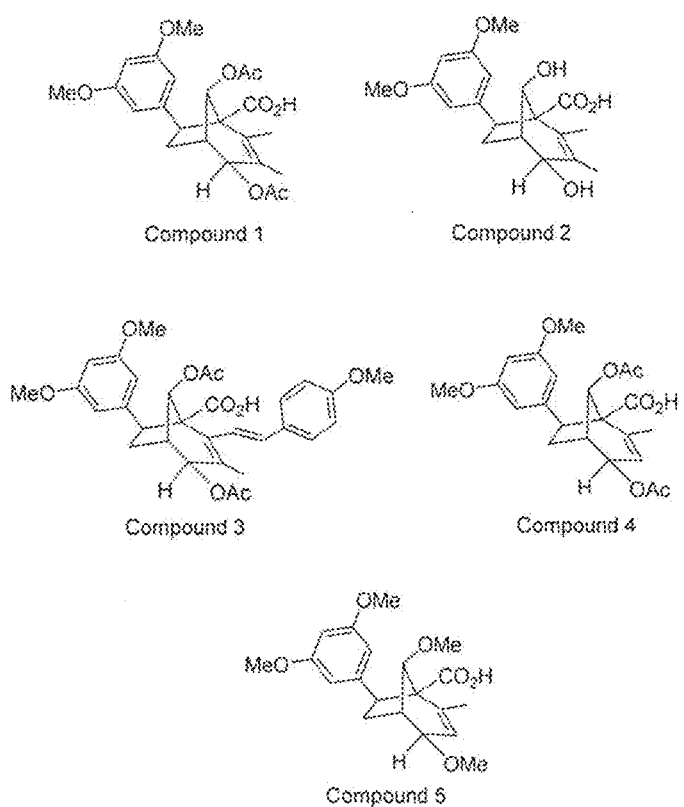

A series of compounds generated using the methods described herein were subjected to a neuromuscular junction (NMJ) postsynaptic transmission assay. Resveratrol was included as a neuroprotectant control. When a wash of hydrogen peroxide (2.25 mM) was introduced, the time to synaptic failure was shortened from approximately 150 min to approximately 40 min (FIG. 2). Introducing resveratrol at 25 nM restored the time to synaptic failure to approximately 150 min upon addition of hydrogen peroxide (2.25 mM).

Of the several initial compounds tested, compounds 1 and 4 emerged as potent neuroprotectants. In this study involving the use of wild-type fruit fly larvae, it was observed that compound 1 (25 nM) allowed the synapse under study to maintain 100% of its normal function even under withering oxidative conditions ($H_2O_2$, 2.25 mM) (FIG. 2). Even a sub-nanomolar concentration of compound 1 (0.5 nM) restored 80% of the time until synaptic failure in the presence of hydrogen peroxide.

Acute oxidative stress triggered by heart attacks, strokes, and traumatic brain injuries causes most of the neurological damage associated with these acute pathologies. Compound 1 and compound 4 (see FIG. 2), both neuroprotective compounds as described herein, are potent non-toxic neuroprotectants that also appear to have ion channel stabilization effects.

Example 2

Resveratrol-Inspired Bridged Bicyclic Compounds as a New Compound Class for the Protection of Synaptic Function From Acute Oxidative Stress While resveratrol protects organisms from the deleterious effects of oxidative stress, its multifarious mechanism of action limits its potential as a selective medicinal agent. To address this shortcoming, a molecular scaffold was designed; compounds containing this scaffold have been termed resveramorphs. The structure of compounds in this class possess much of the functional group characteristics of resveratrol but in a non-planar molecular arrangement and the neuroprotective activities of resveramorph analogs were probed. These novel neuroprotective compounds were found to protect neurotransmission from hydrogen peroxide-induced oxidative stress. These findings demonstrate that, at a subnanomolar level, compounds 1 and 4, protect synaptic transmission from acute oxidative stress at the Drosophila neuromuscular junction. These results position resveramorphs, such as compounds 1 and 4, as potential lead compounds in the development of new drugs for neurodegenerative diseases.

Figure 3:
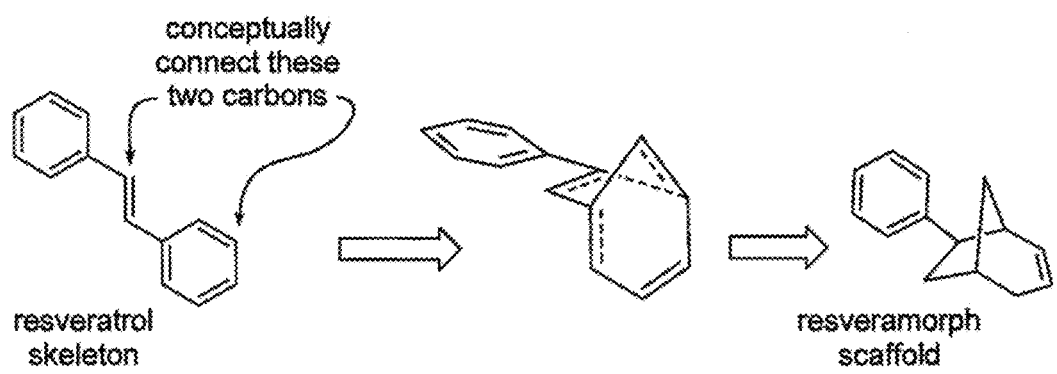
FIG. 3 is an illustration of the resveramorph concept.

In resveratrol, the two oxygen-bearing aryl rings are connected to one another by a two-carbon bridge in a trans orientation. Described herein is a resveratrol-inspired design in which one of the rings, along with the two-carbon bridge, is replaced by a bridged bicycle. One could consider that an aryl unit of resveratrol twists to form a bond (no electrocyclization is intended here) with the ethylene bridge leading to a concave shape (FIG. 3). In this conception, the two-carbon bridge of the bridged bicycle serves as the structural equivalent of the vinyl group in resveratrol. The inspiration to model the two-dimensional structure of resveratrol onto molecules containing a significant amount of three-dimensional structure led to the term "resveramorphs" for the new class of compounds described herein. Among other advantages, replacing an aromatic ring with a bridged bicycle increases the number of $sp^3$ centers without increasing molecular flexibility through rotatable bonds. The resulting compounds are also chiral (though studied here as racemic mixtures) and can be synthesized as single diastereomers. The data presented herein shows that compounds based on the resveramorph conception appear to protect neurotransmission in a fruit fly model under oxidative stress, ultimately offering a new scaffold for future drug development.

Racemic compounds 1 and 2 below bearing the all-carbon resveramorph scaffold were accessed in six to seven synthetic steps.

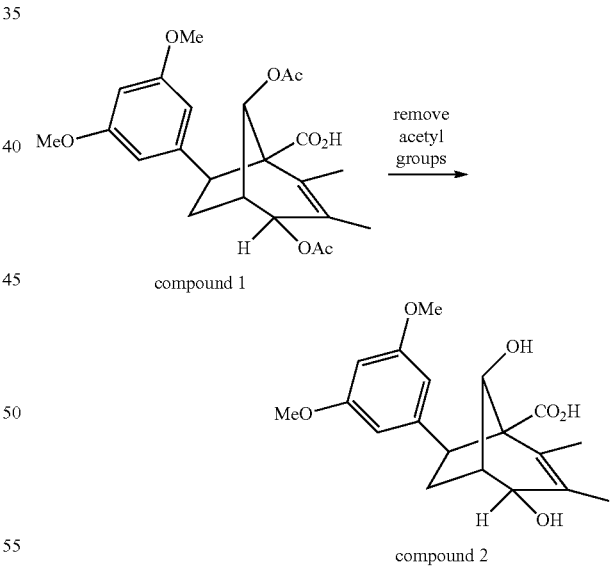

compound 1 compound 2

Figure 4:
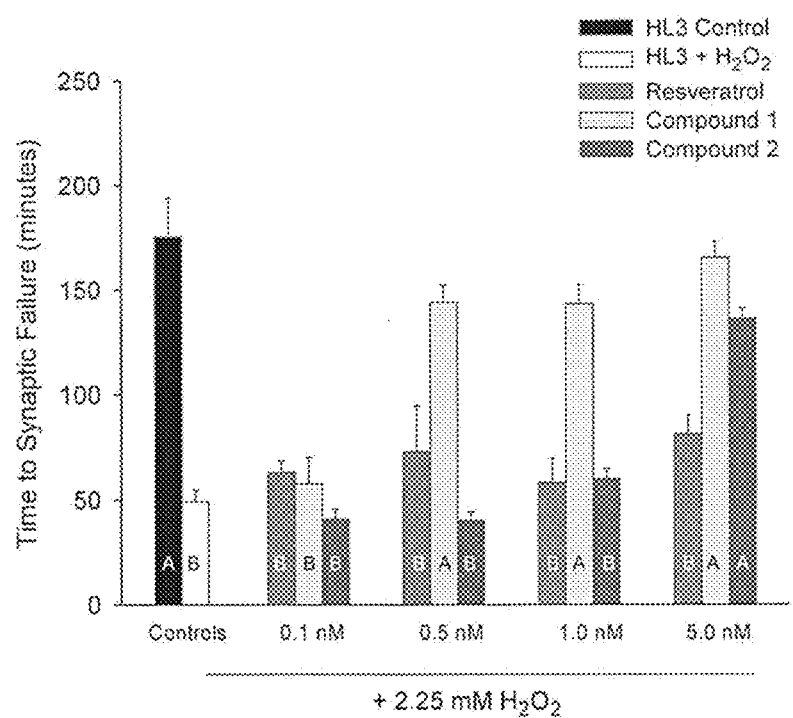
FIG. 4 is a graph showing compound 1 protects synaptic function during acute oxidative stress at low doses. Compound 1 significantly increased time to synaptic failure at the 0.5-5 nM dosage range compared to control and resveratrol-treated preparations [one-way ANOVA, $F(13, 62)=25.04$, $P<0.001$]. Compound 2 similarly increased time to synaptic failure but only at the 5.0 nM dosage [$P<0.001$]. $N=5-9$ larvae per group. Letters in histogram bars represent statistical significance, where different letters indicate statistically significant differences (Holm-Šidák, $P<0.001$) and identical letters indicate non-significance. The letter assignments start with "A" representing the highest mean, followed by "B" indicating the next highest, and so forth. All vertical bar charts are presented as mean±SEM.

To quantify tolerance of neurotransmission to acute oxidative stress, electrophysiological recordings from Drosophila larval preparations were conducted in a hemolymph-like 3 (HL3) saline containing 2.25 mM hydrogen peroxide ($H_2O_2$). Under these conditions, the application of low doses (0.5 nM and 1 nM) of compound 1 significantly increased the amount of time until synaptic failure compared to control larvae that were only treated with saline containing 2.25 mM $H_2O_2$ (FIG. 4). Additionally, compound 1 exerted stronger neuroprotective effects compared to a similar dosage of resveratrol [P<0.001; FIG. 4]. These results establish that compound 1 possesses a neuroprotective effect that is measurably more potent than resveratrol.

Figure 5:
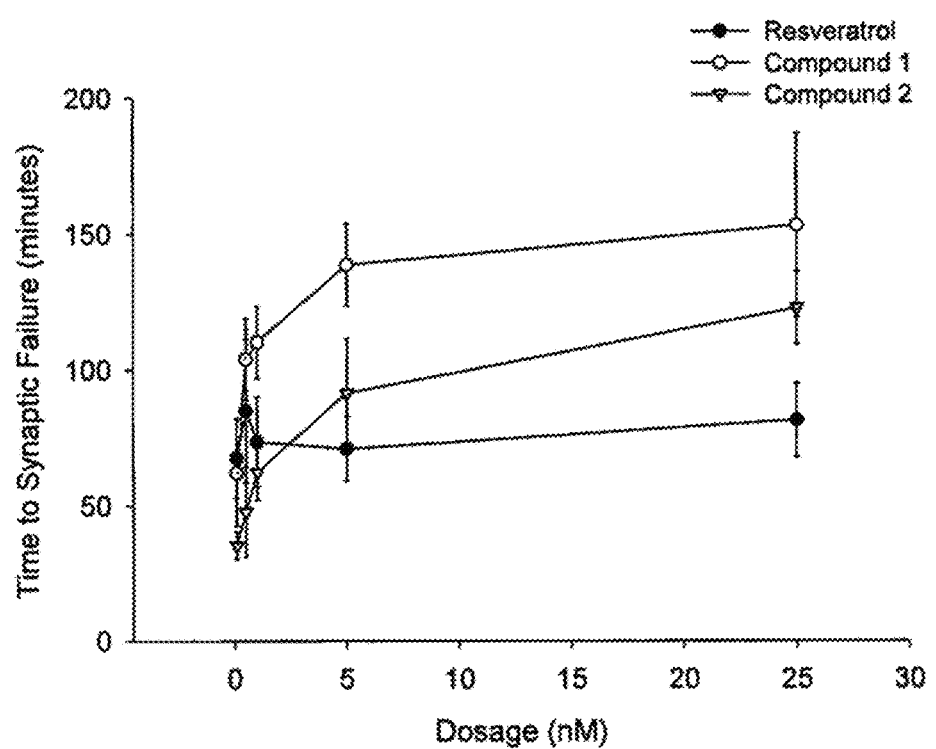
FIG. 5 is a dose-response curve of compounds 1, 2, and resveratrol. $N=6-21$ larvae for each dosage tested.

For further analysis, compound 1 was compared to resveratrol across a broad range of dosage concentrations (FIG. 5). These data reveal that compound 1 possesses stronger neuroprotective effects compared to resveratrol at almost all dosages tested (0.5 nM to 25 nM).

Figure 6:
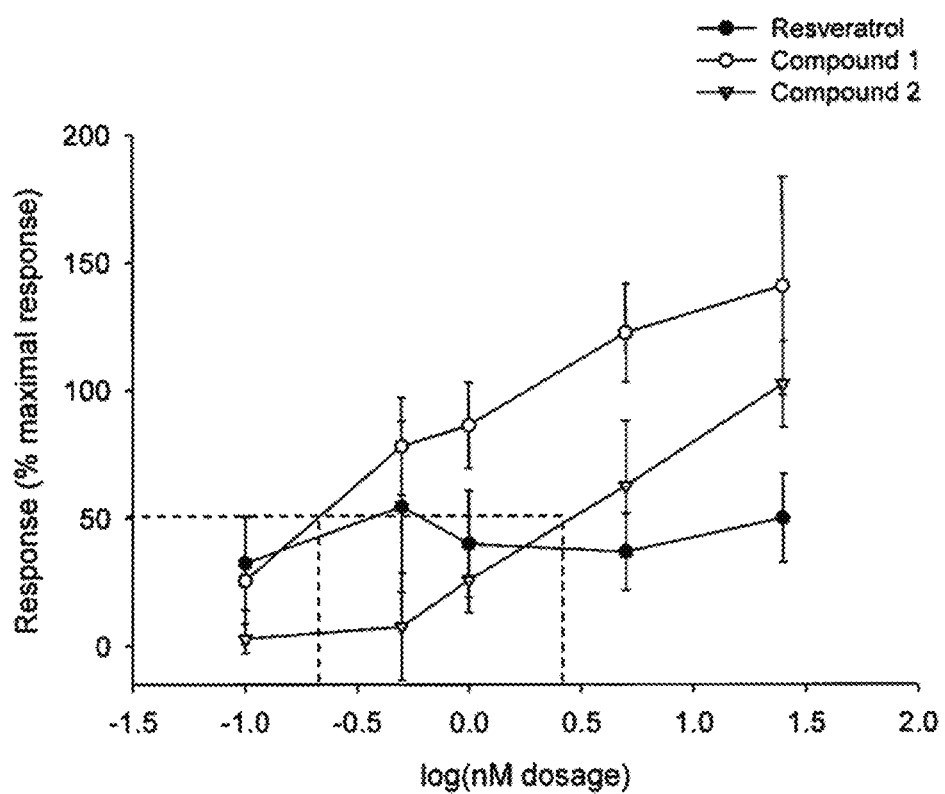
FIG. 6 is a graph showing effective concentration at 50% ($EC_{50}$) determination of compound 1, compound 2, and resveratrol. The $EC_{50}$ of compound 1 was calculated to be 0.21 nM, whereas the $EC_{50}$ of compound 2 was calculated to be 2.99 nM. $N=6-21$ larvae for each dosage tested.

A determination of the $EC_{50}$, or half-maximal effective concentration of compound 1, in protecting neurotransmission from $H_2O_2$ exposure is approximately 0.21 nM. Importantly, compound 1 appears to confer its neuroprotective effects in a dose-dependent manner (FIG. 6). By contrast, the measurements of resveratrol revealed an unusual dose curve, which could not reliably be used to determine its $EC_{50}$. These results indicate that unlike the resveramorph compounds, resveratrol does not act as a neuroprotectant at the chosen dosages.

Figure 7:
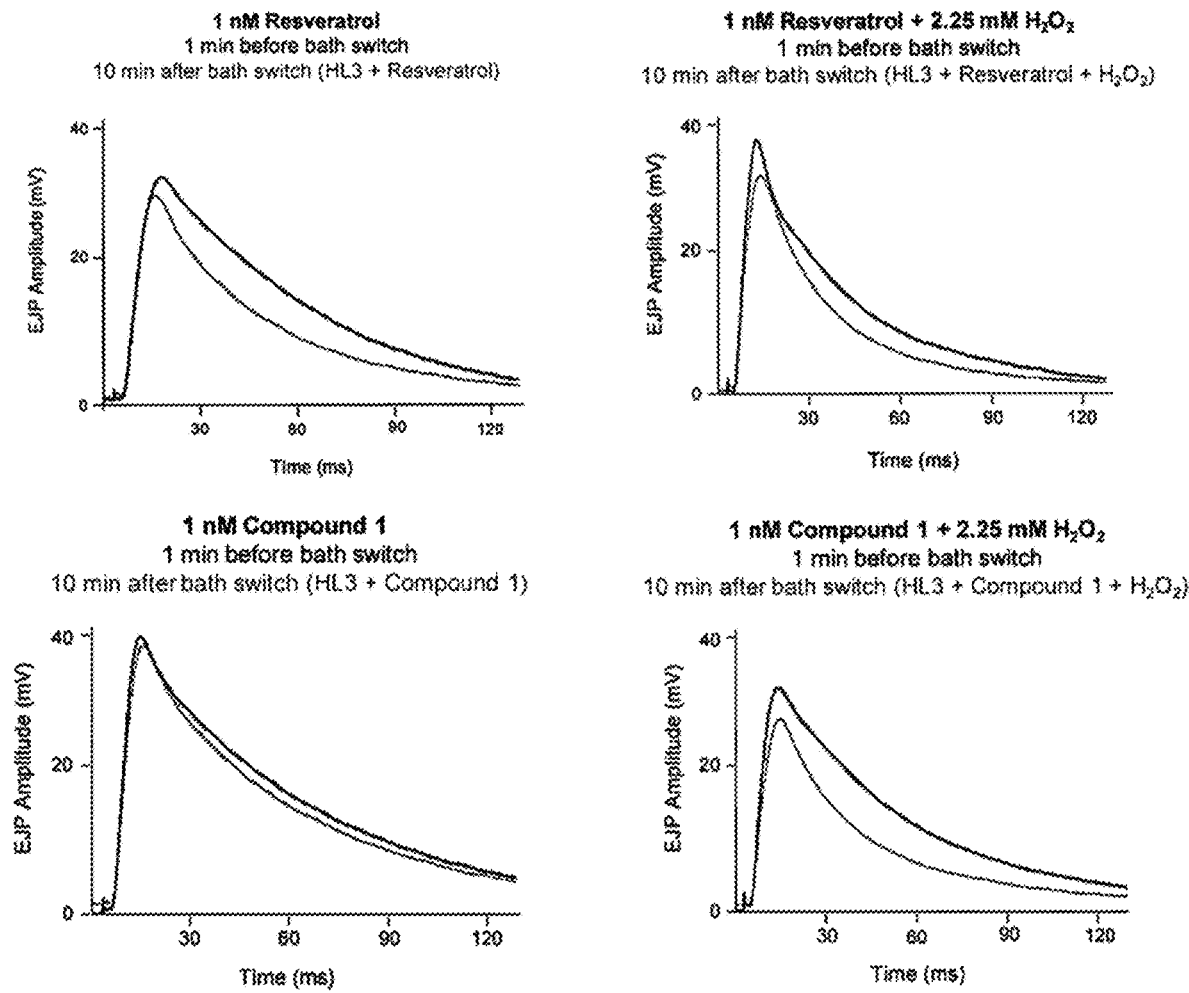
FIG. 7 is a series of graphs showing neuroprotective dosages of resveratrol and compound 1 do not acutely affect characteristic excitatory junction potential (EJP) parameters in the presence and absence of 2.25 mM $H_2O_2$. In all panels, the curved black line represents the average EJP in hemolymph-like saline (HL3) one minute before the recording bath was replaced with HL3 containing the drug alone or the drug and $H_2O_2$. The curved gray line represents the average EJP from the same larvae ten minutes after the bath was switched from HL3 saline to HL3 containing either the drug alone or the drug and $H_2O_2$. The EJP shape was not significantly acutely affected by any of the treatment conditions, confirming that our results are not due to parametric changes in the EJP.

In addition to its well-characterized neuroprotective effects, resveratrol has been shown to modulate neurotransmission at glutamatergic Shaffer collateral-CA1 synapses within the mammalian hippocampus. Specifically, resveratrol inhibits excitatory post-synaptic potentials (EPSPs), which are comparable to excitatory junction potentials (EJP) at the Drosophila NMJ, by desensitizing postsynaptic glutamate receptors. To ensure that the results obtained using compound 1 and resveratrol were not due to changes in the EJP, additional control experiments were performed, as previously described (Caplan et al. J. Neurophys. 109, 649-658). It was found that resveratrol (1 nM) and compound 1 (1 nM) do not have a significant acute effect on the shape or amplitude of the EJP in the presence and absence of 2.25 mM $H_2O_2$ (see FIG. 7). It was also observed that resting membrane potential (RMP) and EJP amplitude decline in larvae treated with $H_2O_2$ alone and $H_2O_2$ with 1 nM compound 1 (see FIGS. 8A. 8B). Interestingly, the administration of compound 1 significantly slowed the decline of RMP, potentially contributing to the protection of synaptic transmission (see FIG. 8A).

The work described herein sought to determine if the activity of compound 1 would be sensitive to a profound structural modification that was easily accomplished synthetically. To this end, the acetyl groups present in compound 1 were removed to reveal the hydroxyl groups of compound 2, which are capable of acting as potent hydrogen bond donors. Not surprisingly, compound 2 exhibited substantially different activity from compound 1. At low doses (0.1 nM and 0.5 nM), compound 2 did not prolong time to failure during $H_2O_2$ exposure (FIG. 4)). However, at higher doses, compound 2 significantly increased time to synaptic failure during $H_2O_2$ exposure compared to control preparations [P<0.001; FIG. 4)]. In contrast, compound 1 exhibited strong neuroprotective effects under these conditions when administered at doses as low as 500 pM (FIG. 4)). Also, the $EC_{50}$ of compound 2 was calculated to 2.99 nM, which is over ten-fold higher than compound 1 (FIG. 6)).

In conclusion, the present findings suggest that the resveramorph scaffold serves as a promising starting point in the development of novel neuroprotective compounds. These studies clearly indicate dose-dependent protection of neurotransmission from acute oxidative stress. The protective property also appears to depend on the functional groups that adorn the resveramorph scaffold.

Methods

Animals

Wandering third instar larvae (≈110 hours old) from the fruit fly, Drosophila melanogaster, were utilized for all electrophysiological experiments described throughout this study. Larvae were reared at 25° C. on 12 h:12 h light-dark (LD) cycles in an incubator. Only $w^{1118}$ larvae were utilized in this study.

Electrophysiology

All electrophysiological experiments were performed as previously described with the exception of the resistance of the intracellular electrodes (60-90 MΩ) (Caplan et al. J. Neurophys. 109, 649-658). Excitatory junction potentials (EJPs) were elicited via repetitive stimulation (0.3 ms pulses delivered suprathreshold at a frequency of 1 Hz) and measured until synaptic failure occurred, which was characterized by an EJP amplitude of <1 mV being recorded. Electrophysiological recordings from larval preparations were conducted in hemolymph-like 3 (HL3) saline containing 2.25 mM $H_2O_2$. Preparations that took a greater amount of time to reach synaptic failure in HL3 saline containing 2.25 mM $H_2O_2$ possessed a higher tolerance for acute oxidative stress compared to preparations that took a lesser amount of time to reach stimulus-induced synaptic failure. HL3 saline containing 1.5 mM $Ca^{2+}$ and 20 mM $Mg^{2+}$ was used as the recording saline throughout this study. HL3 has been utilized by other research groups to record EJPs.[20] Intracellular recordings of resting membrane potential were taken from Drosophila larval muscle 6.

Pharmacology

All test compounds and $H_2O_2$ were applied to the Drosophila larval NMJ preparation as previously described by Caplan et al. (supra). However, the compounds utilized in the Caplan et al. work were dissolved in dimethyl sulfoxide (DMSO), whereas the compounds utilized in the present study are water-soluble at the concentrations used and thus were dissolved in $ddH_2O$.

Statistics

The statistics utilized in the vertical bar charts and line graphs were performed as previously described with the exception of the error bars being presented as mean±SEM instead of mean±SD. The $EC_{50}$, or half maximal effective concentration, of each test compound was determined by plotting the logio(compound dose) against the corresponding average percentage of the maximal effectiveness, as previously described (Caplan et al. J. Neurophys. 109, 649-658). A line was drawn to connect all of the data points for each compound; the point on the line at which a compound reached 50% efficacy was determined for each compound, and the inverse log of this value was calculated and determined to be the $EC_{50}$ dosage for compounds 1 and 2, as well as resveratrol—see Equations (Determination of % maximal response of resveratrol and resveramorphs) below:

$$[TSF \text{ of preparation (HL3, } H_2O_2, \text{ specific dose of drug)}] - [\text{average } TSF \text{ of HL3 } H_2O_2 \text{ control larvae}] = \text{Value } A \quad \text{EQUATION 1}$$

$$[\text{Value } A]/[(\text{average } TSF \text{ of HL3 control larvae}) - (\text{average } TSF \text{ of HL3 } H_2O_2 \text{ control larvae})] = \text{Value } B \quad \text{EQUATION 2}$$

$$(\text{Value } B)(100) = \% \text{ maximal response of a single preparation} \quad \text{EQUATION 3}$$

TSF=time to synaptic failure (minutes)
Average TSF of HL3 $H_2O_2$ control larvae=41.67 minutes
[(average TSF of HL3 control larvae)−(average TSF of HL3 $H_2O_2$ control larvae)]=79.25 minutes General Information Reactions were carried out under an argon atmosphere in oven-dried glassware with magnetic stirring (unless otherwise stated). Purification of reaction products was carried out using flash silica gel 40-63 μm. Analytical thin-layer chromatography was performed on 200 μm silica gel 60 F-254 plates. Visualization of TLC plates was accomplished with UV light, followed by staining with vanillin or potassium permanganate and drying with a heat gun. $^1$H NMR spectra were recorded on a 400 MHz spectrometer and are reported in parts per million (ppm) using solvent as an internal standard ($CDCl_3$ at 7.26 ppm). Data are reported as b=broad, s=singlet, d=doublet, t=triplet, q=quartet, p=pentet, m=multiplet; coupling constants in hertz (Hz). $^{13}C\{^1H\}$ NMR were recorded on a 100 MHz spectrometer. Chemical shifts are reported in ppm, using solvent as an internal standard ($CDCl_3$ at 77.0 ppm). High-resolution mass spectra were recorded by an ESI-TOF MS spectrometer or a DART-TOF spectrometer. All reagents were purchased from commercially available sources and were used without further purification. All solvents were dried over activated 3 Å molecular sieves except for THF, which was dried by passing through an activated alumina filter.

Synthesis of ethyl 5-(3,5-dimethoxyphenyl)-2-oxo-cyclopentanecarboxylate (intermediate 1)

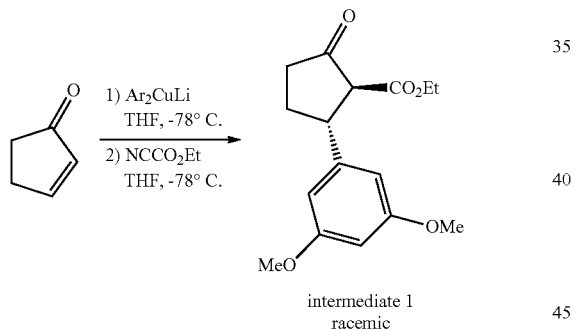

A flame-dried flask was affixed with an addition funnel and charged with tetrahydrofuran (200 mL). Under argon, 1-bromo-3,5-dimethoxybenzene (2 eq, 17.3 g, 80.0 mmol) was added. The vessel was cooled to −78° C. using a dry ice/acetone bath and n-butyl lithium (2 eq, 50 mL, 1.6 M in hexane, 80 mmol) was added dropwise. After stirring for 1 hour at −78° C., copper cyanide (1 eq, 3.60 g, 40.2 mmol) was added. This was stirred at −78° C. and then the dry ice bath was removed to ensure complete dissolution of the copper cyanide with 10 min additional stirring. The dry ice bath was returned and the reaction was stirred at −78° C. for 10 min longer. Cyclopent-2-enone (1 eq, 3.30 mL, 39.4 mmol) was added dropwise as a solution in tetrahydrofuran (5 mL) through the septum over 20 min. The solution turned yellow in color and was left stirring at −78° C. temperature for 2 hours. Ethyl cyanoformate (2.1 eq, 8.00 mL, 80.9 mmol) was added neat and the reaction was stirred at −78° C. for an additional 5 hours. The reaction was quenched with saturated aqueous ammonium chloride (200 mL). The product was extracted twice from the organic layer with diethyl ether (200 mL), the combined organic layers were dried using sodium sulfate, and then concentrated in vacuo. The crude product was purified via silica gel chromatography with ethyl acetate in hexanes (2:8) as eluent led to semi-pure intermediate 1 as a pinkish oil (5.26 g) in 45% yield. $^1$H NMR: 6.43-6.41 (m, 2H), 6.37-6.35 (m, 1H), 4.25-4.13 (m, 2H), 3.78 (s, 6H), 3.75-3.69 (m, 1H), 3.30 (d, J=12.0 Hz, 1H), 2.70-2.51 (m, 1H), 2.50-2.36 (m, 2H), 2.07-1.93 (m, 1H), 1.25 (t, J=7.1 Hz, 3H). $^{13}$C NMR: 210.6, 168.7, 161.1, 143.6, 105.1, 98.8, 62.3, 61.6, 55.3, 46.3, 38.6, 28.8, 14.2. HRMS: theoretical [M+H]$^+$293.1384, found 293.1387.

Synthesis of 2-trimethylsilylethyl 5-(3,5-dimethoxyphenyl)-2-oxocyclopentanecarboxylate (intermediate 2)

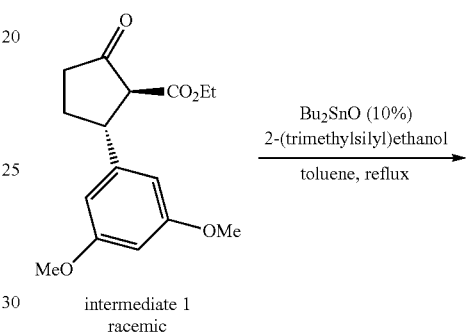

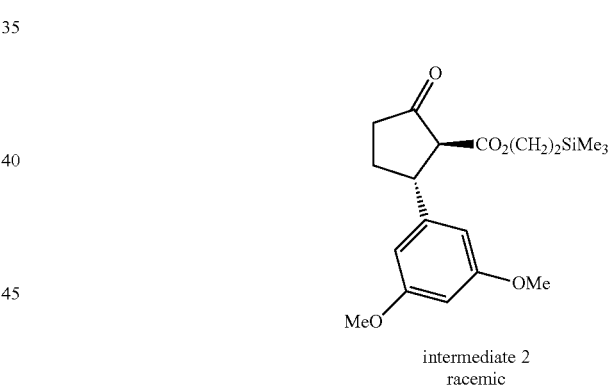

A round bottom flask was affixed to a jacketed reflux condenser and charged with toluene (160 mL). Intermediate 1 (1 eq, 4.50 g, 15.4 mmol) was added to the flask along with dibutyltin oxide (0.1 eq, 0.396 g, 1.59 mmol) and 2-(trimethylsilyl)ethanol (2.7 eq, 6.00 mL, 41.9 mmol) and the solution was refluxed. After 24 hours, the solvent was removed in vacuo and the crude product was purified by silica gel chromatography using ethyl acetate in hexanes (2:8), giving intermediate 2 as an amber colored liquid (2.46 g) in 44% yield. $^1$H NMR: 6.42 (d, J=2.2 Hz, 2H), 6.35 (t, J=2.2 Hz, 1H), 4.25-4.14 (m, 2H), 3.78 (s, 6H), 3.76-3.66 (m, 1H) 3.29 (d, J=12.0 Hz, 1H), 2.62-2.52 (m, 1H), 2.51-2.37 (m, 2H), 2.04-1.91 (m, 1H), 0.98 (dd, J=7.2, 10.5 Hz, 2H), −0.01 (s, 9H). $^{13}$C NMR: 210.7, 168.9, 161.1, 143.5, 105.1, 98.8, 63.9, 62.5, 55.3, 46.4, 38.2, 28.8, 17.4, −1.4, −1.6. HRMS: theoretical [M+H]$^+$365.1779, found 365.1767.

Synthesis of 2-trimethylsilylethyl-1-(3,5-dimethoxyphenyl)-6,7-dimethyl-5-oxo-4-oxa-2,7a-dihydro-1H-indene-7a-carboxylate (intermediate 5)

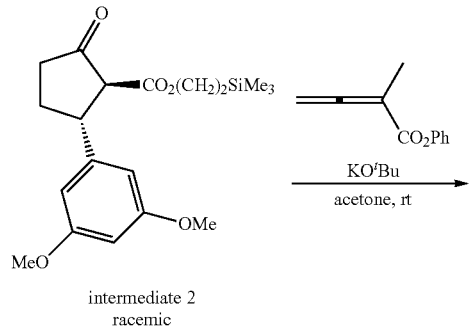

intermediate 2
racemic intermediate 5
racemic

To a solution of intermediate 2 (1 eq, 0.583 g, 1.60 mmol) in acetone (10 mL) was added potassium tert-butoxide (0.1 eq, 0.018 g, 0.160 mmol) and stirred for 15 minutes until a color change to yellow was observed. To this was added as solution of phenyl 2-methylbuta-2,3-dienoate (Bhat et al. J. Org. Chem. 79, 9402) (1.1 eq, 0.295 g, 1.69 mmol) in acetone (1.7 mL). It is critical to use the 10% excess of the allenoate indicated here to drive the reaction towards formation of the lactone product. The reaction mixture was stirred at room temperature overnight. Upon reaction completion (as monitored by TLC), the solvent was removed in vacuo. Crude products were purified using silica gel chromatography with ethyl acetate in hexanes (3:7) to give intermediate 5 as a yellow oil (0.456 g) with a slight amount of inseparable side product. The approximate yield of 5 was 64%. $^1$H NMR: 6.47 (d, J=2.2 Hz, 2H), 6.36 (t, J=2.2 Hz, 1H), 5.52 (dd, J=1.9, 3.0 Hz, 1H), 4.07-3.99 (m, 2H), 3.76 (s, 6H), 3.57 (t, J=8.6 Hz, 1H), 2.75 (ddd, J=1.6, 9.0, 15.6 Hz, 1H), 2.65 (ddd, J=3.1, 8.2, 15.7 Hz, 1H), 2.09 (s, 3H), 1.91 (s, 3H), 0.88-0.69 (m, 2H), −0.02 (s, 9H). $^{13}$C NMR: 169.8, 162.4, 160.6, 152.6, 148.3, 141.9, 122.4, 109.2, 107.7, 98.8, 64.2, 60.0, 55.2, 53.9, 35.4, 17.3, 17.0, 13.4, −1.8. HRMS: theoretical [M+H]$^+$445.2041, found 445.2062.

Synthesis of 2-trimethylsilylethyl-7-(3,5-dimethoxyphenyl)-4,8-dihydroxy-2,3-dimethylbicyclo[3.2.1]oct-2-ene-1-carboxylate (intermediate 7)

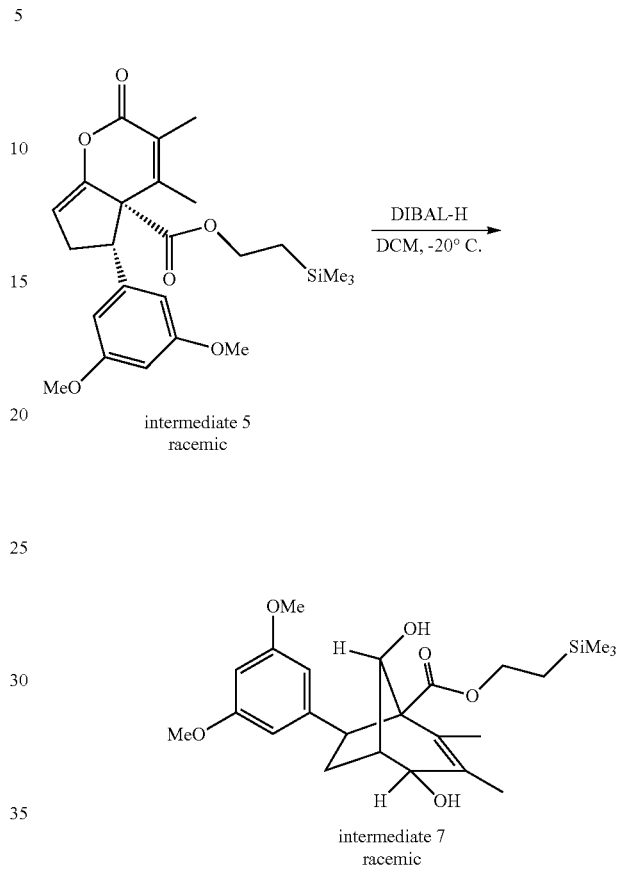

intermediate 5
racemic intermediate 7
racemic

To a solution of lactone intermediate 5 (1 eq, 0.098 g, 0.22 mmol) in dichloromethane (2.5 mL) at −20° C. was added diisobutyl aluminum hydride (3 eq, 0.66 mL, 1M in toluene, 0.66 mmol) and the reaction mixture was stirred at 0° C. for 3 h. The reaction was worked up with aqueous hydrochloric acid (3 N, 4 mL), returning to room temperature for 1 hour. The solution turned yellow upon workup. The organic compounds were extracted with dichloromethane (4 mL) three times and dried over anhydrous sodium sulfate, and solvent was removed in vacuo. The crude products were purified using silica gel chromatography using ethyl acetate in hexanes (3:7) to give the pure product intermediate 7 as a clear oil (0.048 g) and as a single diastereomer in 49% yield. $^1$H NMR: 6.27 (s, 3H), 4.86 (d, J=5.9 Hz, 1H), 3.92 (dtd, J=7.3, 10.7, 17.6 Hz, 2H) 3.75 (s, 6H), 3.71 (s, 1H), 3.54 (d, J=11.7 Hz, 1H), 3.15 (dd, J=4.4, 10.3 Hz, 1H), 2.71-2.64 (m, 1H), 1.93 (ddd, J=4.4, 7.3, 14.2 Hz, 1H), 1.88-1.81 (m, 1H), 1.86 (s, 3H), 1.73 (s, 3H), 0.66-0.53 (m, 2H), −0.05 (s, 9H). $^{13}$C NMR: 174.7, 160.5, 147.2, 129.7, 127.3, 107.0, 97.5, 76.4, 74.8, 62.9, 61.7, 55.2, 51.3, 40.4, 32.9, 16.9, 16.7, 15.6, −1.8. HRMS: theoretical [M+Na]$^+$ 471.2173, found 471.2196.

Synthesis of 2-trimethylsilylethyl-7-(3,5-dimethoxyphenyl)-4,8-diacetoxy-2,3-dimethylbicyclo[3.2.1]oct-2-ene-1-carboxylate (intermediate 8)

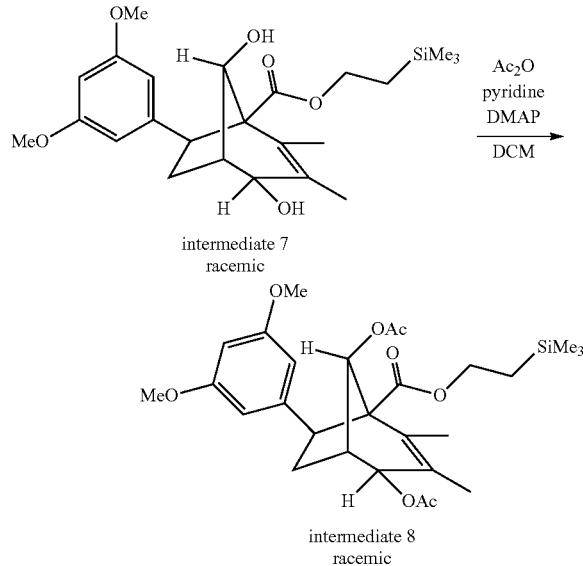

Intermediate 7 (1 eq, 0.044 g, 0.098 mmol) was dissolved in dichloromethane (1.5 mL) and acetic anhydride (5 eq, 0.046 mL, 0.49 mmol), 4-dimethylamino pyridine (1 small crystal, approximately 0.1 eq), and pyridine (5 eq, 0.028 mL, 0.49 mmol) were added with stirring at room temperature. The reaction was stirred until thin layer chromatography revealed complete conversion of the starting material to a less polar product (approximately 16 hours). Solvent was removed in vacuo and the crude product was purified via silica gel chromatography with ethyl acetate in hexanes (3:7) to afford pure intermediate 8 as a clear oil (0.045 g) in 87% yield. $^1$H NMR: 6.29 (d, J=1.6 Hz, 2H), 6.27 (t, J=1.6 Hz, 1H), 5.51 (d, J=5.5 Hz, 1H), 4.99 (s, 1H), 3.83-3.61 (m, 2H,), 3.74 (s, 6H), 3.15 (dd, J=5.9, 9.8 Hz, 1H), 2.96-2.89 (m, 1H), 2.13-2.07 (m, 2H), 2.05 (s, 3H), 2.02 (s, 3H), 1.90 (s, 3H) 1.70 (s, 3H), 0.55 (dd, J=8.0, 10.0 Hz, 2H), −0.07 (s, 9H). $^{13}$C NMR: 171.1, 170.62, 170.61, 160.6, 146.0, 133.7, 124.4, 106.7, 98.2, 76.3, 74.3, 62.6, 60.8, 55.3, 52.7, 37.4, 33.2, 21.3, 21.1, 16.8, 16.5, 16.3, −1.76. HRMS: theoretical [M+NH$_4$]$^+$550.2831, found 550.2813

Synthesis of 7-(3,5-dimethoxyphenyl)-4,8-diacetoxy-2,3-dimethylbicyclo[3.2.1]oct-2-ene-1-carboxylic acid (compound 1)

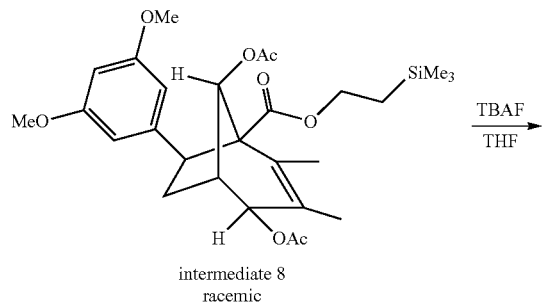

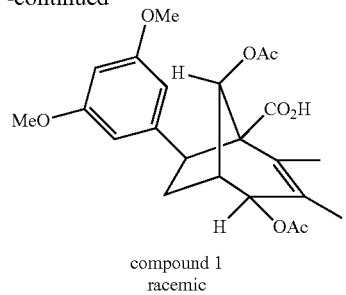

To a stirred solution of compound 8 (1 eq, 0.014 g, 0.026 mmol) dissolved in tetrahydrofuran (1.0 mL) was added tetrabutylammonium fluoride solution (9 eq, 0.13 mL, 1 M in THF, 0.13 mmol) and the reaction was stirred at room temperature for 1 h. Upon reaction completion (as monitored by thin layer chromatography), the reaction was quenched with saturated ammonium chloride solution (1 mL) and the organic product was extracted twice with ethyl acetate (2 mL). The solvents were removed in vacuo and the remaining residue was purified using silica gel chromatography with ethyl acetate in hexanes (3:7) to afford pure compound 1 as a white solid (0.010 g) in 89% yield. $^1$H NMR: 6.33 (d, J=2.0 Hz, 2H), 6.26 (t, J=2.0 Hz, 1H), 5.50 (d, J=5.1 Hz, 1H), 4.99 (s, 1H), 3.74 (s, 6H), 3.14 (dd, J=5.5, 9.8 Hz, 1H), 2.96-2.91 (m, 1H), 2.15-2.02 (m, 2H), 2.06 (s, 3H), 2.02 (s, 3H), 1.91 (s, 3H), 1.70 (s, 3H). $^{13}$C NMR: 173.4, 171.2, 170.7, 160.4, 146.4, 133.7, 124.3, 106.6, 98.4, 76.4, 74.4, 61.0, 55.2, 52.4, 37.3, 33.4, 21.3, 21.1, 16.41, 16.38. HRMS: theoretical [M+Na]$^+$455.1676, found 455.1685.

Synthesis of 7-(3,5-dimethoxyphenyl)-4,8-dihydroxy-2,3-dimethylbicyclo[3.2.1]oct-2-ene-1-carboxylic acid (compound 2)

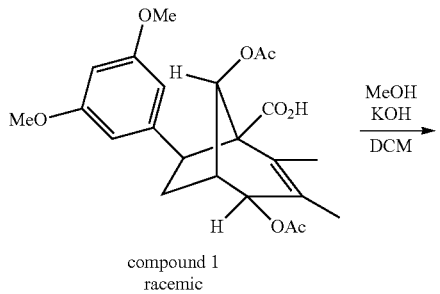

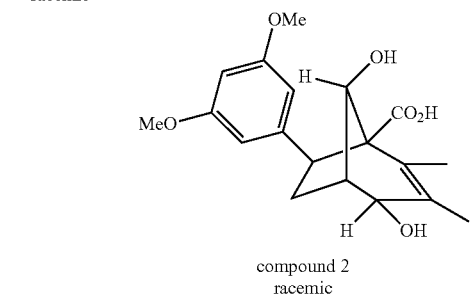

Compound 1 (1 eq, 0.010 g, 0.023 mmol) was dissolved in dichloromethane (0.8 mL) and then methanol (0.8 mL) was added at room temperature under air. After 5 min of stirring, potassium hydroxide (0.16 mL, 10% w/w aqueous) was added and the reaction was left stirring for 16 hours. Hydrochloric acid (10% w/w aqueous) was added dropwise until litmus paper indicated a pH of approximately one. Ethyl acetate was added to dilute the reaction and the addition of a small amount of brine separated the aqueous and organic layers. The organic layer was dried over sodium sulfate and filtered; the solvent was then removed in vacuo. Compound 2 was passed through a silica gel plug using ethyl acetate and isolated as a residue (7.5 mg, 0.021 mmol) in 91% yield. $^1$H NMR: 6.32 (d, J=2.2 Hz, 2H), 6.27 (t, J=2.2 Hz, 1H), 4.86 (d, J=5.9 Hz, 1H), 3.76 (s, 6H), 3.62 (s(b), 1H), 3.14 (dd, J=4.0, 9.8 Hz, 1H), 2.71-2.65 (m, 1H), 1.97-1.89 (m, 2H), 1.87 (s, 3 H), 1.77 (s, 3 H). $^{13}$C NMR: 160.4, 147.2, 128.9, 128.5, 127.8, 107.2, 97.7, 76.4, 74.2, 62.0, 55.3, 50.5, 40.0, 32.7, 16.9, 15.4. HRMS: theoretical [M+Na]$^+$371.1465, found 371.1471.

Synthesis of 2-trimethylsilyethyl 2-[(E)-2-(p-methoxyphenyl)ethenyl)]-7-(3,5-dimethoxyphenyl)-4,8-dihydroxy-3-methylbicyclo[3.2.1]oct-2-ene-1-carboxylate (intermediate 10)

room temperature for 1 hour. The solution turned yellow upon workup. The organic compounds were extracted with dichloromethane (4 mL) three times and dried over anhydrous sodium sulfate, and solvent was removed in vacuo from the organic extracts. The crude products were purified using silica gel chromatography using ethyl acetate/hexanes (3:7) to give intermediate 10 as a clear oil (0.039 g) and as a single diastereomer in a 5% two-step yield. $^1$H NMR: 7.32 (d, J=8.6 Hz, 2H), 6.86 (d, J=8.2 Hz, 2H), 6.51-6.26 (m, 5H), 4.93 (d, J=5.5 Hz, 1H), 3.89-3.71 (m, 2H), 3.80 (s, 3H), 3.76 (s, 6H), 3.68 (s, 1H) 3.37 (dd, J=3.9, 9.4 Hz, 1H), 2.76-2.72 (m, 1H), 2.01 (s, 3H), 1.99-1.83 (m, 2H), 0.55-0.46 (m, 2H), 0.02-0.25 (m, 9H). $^{13}$C NMR: 174.4, 160.4, 159.3, 146.9, 133.0, 132.2, 131.1, 129.9, 127.3, 123.3, 114.0, 107.1, 97.5, 76.6, 74.6, 62.9, 61.3, 55.3, 55.2, 51.4, 40.3, 32.7, 18.3, 17.1, −1.9. HRMS: theoretical [M+Na]$^+$589.2592, found 589.2593.

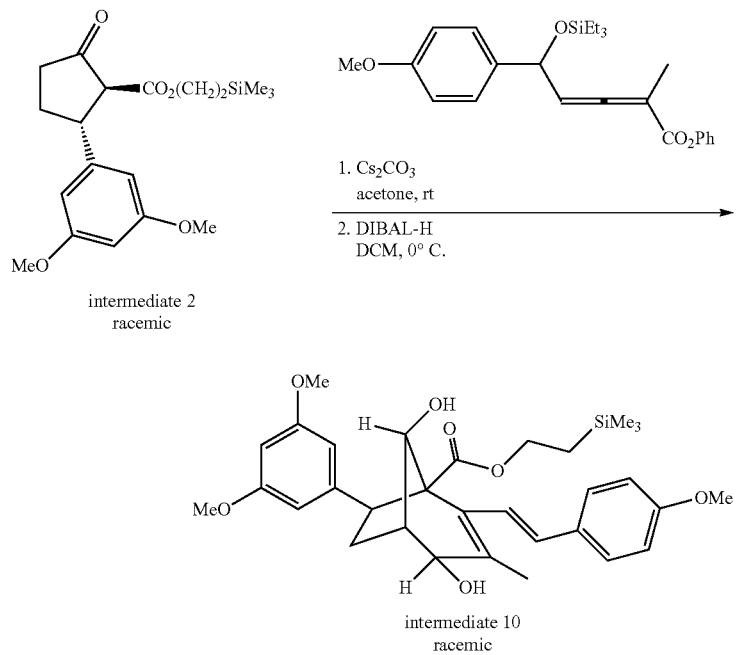

To a solution of intermediate 2 (1 eq, 0.146 g, 0.4 mmol) in acetone (4 mL) was added cesium carbonate (1.1 eq, 0.143 g, 0.44 mmol) and stirred for 15 min until a color change to yellow was observed. To this was added phenyl 5-(4-methoxyphenyl)-2-methyl-5-(triethylsilyloxy)penta-2,3-dienoate (1.1 eq, 0.187 g, 0.44 mmol). It is critical to use the 10% excess of the allenoate indicated here to drive the reaction towards lactone formation. The reaction mixture was stirred at room temperature overnight. Upon reaction completion (as monitored by TLC), the solvent was removed in vacuo. Crude products were purified using silica gel chromatography with ethyl acetate/hexanes (3:7) to give a yellow oil (0.077 g) with a slight amount of inseparable side product. To a solution of this intermediate in dichloromethane (3 mL) at 0° C. was added diisobutyl aluminum hydride (3 eq, 0.78 mL, 1 M solution in toluene) and the reaction mixture was stirred at 0° C. for 4 h. The reaction was worked up with aqueous hydrochloric acid (4 mL, 3 N), returning to Synthesis of 2-trimethylsilylethyl 2-[(E)-2-(p-methoxyphenyl)ethenyl)]-7-(3,5-dimethoxyphenyl)-4,8-diacetoxy-3-methylbicyclo[3.2.1]oct-2-ene-1-carboxylate (intermediate 11)

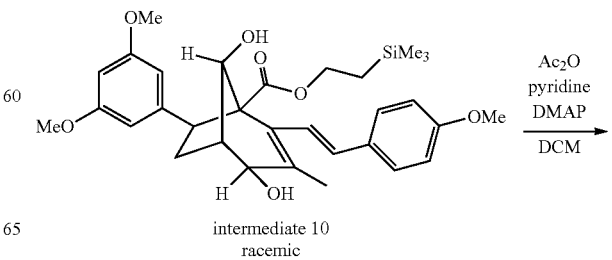

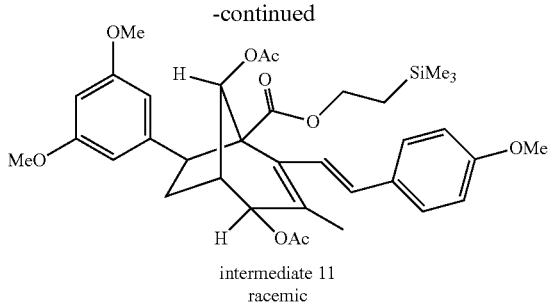

intermediate 11
racemic

Intermediate 10 (1 eq, 0.043 g, 0.076 mmol) was dissolved in dichloromethane (1 mL) and acetic anhydride (5 eq, 0.033 mL, 0.38 mmol), 4-dimethylamino pyridine (1 small crystal, approximately 0.1 eq), and pyridine (5 eq, 0.03 mL, 0.38 mmol) were added with stirring at room temperature. The reaction was stirred until thin layer chromatography revealed complete conversion of the starting material to a less polar product (approximately 16 hours). Solvent was removed in vacuo and the crude product was purified via silica gel chromatography with ethyl acetate/hexanes (3:7) to afford pure intermediate 11 as a clear oil (0.046 g) in 93% yield. $^1$H NMR: 7.36 (d, J=8.6 Hz, 2H); 6.87 (d, J=8.6 Hz, 2H), 6.36-6.26 (m, 5H), 5.56 (d, J=5.1 Hz, 1H), 5.12-5.10 (b, 1H), 3.81 (s, 3H), 3.75 (s, 6H), 3.74-3.67 (m, 1H), 3.64-3.54 (m, 1H), 3.34 (dd, J=6.3, 9.4 Hz, 1H), 3.02-2.97 (m, 1H), 2.22-2.11 (m, 2H) 2.10 (s, 3H), 2.06 (s, 3H), 1.84 (s, 3H), 0.53-0.41 (m, 2H), 0.00-0.17 (m, 9H). $^{13}$C NMR: 171.2, 170.5, 170.2, 160.5, 159.3, 145.6, 137.0, 132.5, 130.0, 127.4, 127.0, 124.2, 114.0, 106.8, 98.2, 76.3, 74.2, 62.5, 60.9, 55.3, 55.2, 52.8, 37.5, 33.1, 21.3, 21.1, 17.9, 16.9, −1.8.

Synthesis of 2-[(E)-2-(p-methoxyphenyl)ethenyl]-4,8-diacetoxy-7-(3,5-dimethoxyphenyl)-3-methylbicyclo[3.2.1]oct-2-ene-1-carboxylic acid (compound 3)

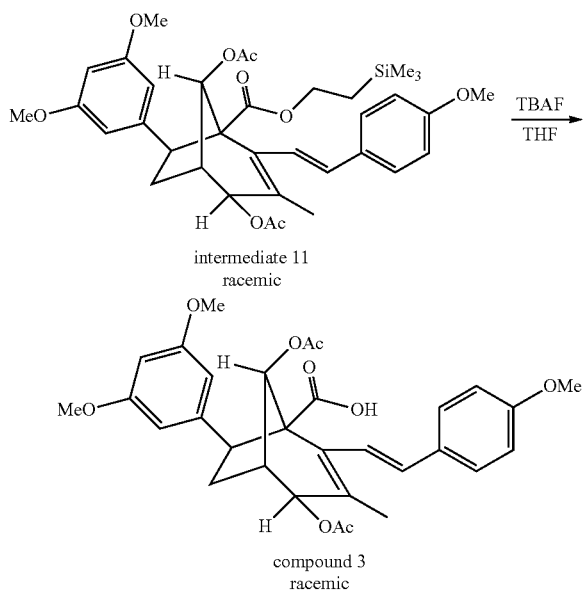

To a stirred solution of intermediate 11 (1 eq, 0.046 g, 0.071 mmol) dissolved in tetrahydrofuran (1.0 mL) was added tetrabutylammonium fluoride in tetrahydrofuran (2 eq, 0.14 mL, 1 M) and the reaction was stirred at room temperature for approximately 16 h. Upon reaction completion (as monitored by thin layer chromatography), the reaction was quenched with saturated ammonium chloride solution (1 mL) and the organic product was extracted twice with ethyl acetate (2 mL). The solvents were removed in vacuo and the remaining residue was purified using silica gel chromatography with ethyl acetate/hexanes (3:7) to afford pure compound 3 as a white solid (0.026 g) in 66% yield. $^1$H NMR: 7.36 (d, J=9.0 Hz, 2H), 6.98 (d, J=16 Hz, 1H), 6.82 (d, J=8.6 Hz, 2H), 6.41 (d, J=2.0 Hz, 2H), 6.27 (d, J=16.4 Hz, 1H), 6.20 (t, J=2.4 Hz, 1H), 5.53 (d, J=5.1 Hz, 1H), 5.13-5.09 (b, 1H), 3.80 (s, 3H), 3.73 (s, 6H), 3.26 (dd, J=5.8 Hz, 9.8 Hz, 1H), 3.00-2.94 (m, 1H), 2.09 (s, 3H), 2.05 (s, 3H), 2.04-1.94 (m, 2H), 1.85 (s, 3H). $^{13}$C NMR: 174.3, 171.6, 170.7, 160.0, 158.7, 148.9, 140.0, 131.0, 130.5, 127.3, 127.0, 125.2, 113.7, 106.4, 97.9, 77.5, 75.5, 61.9, 58.8, 55.3, 55.1, 37.9, 33.9, 21.7, 21.2, 18.1.

Other Embodiments

Any improvement may be made in part or all of the neuroprotective compounds, compositions, and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:
1. A compound of Formula 1:

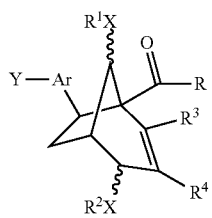

or an enantiomer, diastereomer, racemic mixture or a pharmaceutically acceptable salt or solvate thereof, wherein:
Ar is aryl;
Y is an ortho, meta, or para aryl substituent selected from the group consisting of alkyl, alkyloxy, alkylamino, NR$^5$R$^6$, and halo;
X is O, S, or NH bonded to R$^1$ or R$^2$;
R is H, alkyl, aryl, OH, alkyloxy, aryloxy, NH$_2$, alkylamino, NR$^5$R$^6$, or arylamino;

$R^1$ and $R^2$ are alkylcarbonyl, arylcarbonyl, alkyl, or H, individually;

$R^3$ is arylCH=CH, alkylCH=CH, or alkyl;

$R^4$ is H, alkyl, or aryl; and $R^5$ and $R^6$ are alkyl, individually.

2. The compound of claim 1, wherein:

alkyl is a saturated hydrocarbon moiety containing up to six carbons at any of Y, R, $R^1$, $R^2$, $R^3$, $R^4$, $R^5$ and $R^6$.

3. The compound of claim 1, having the formula:

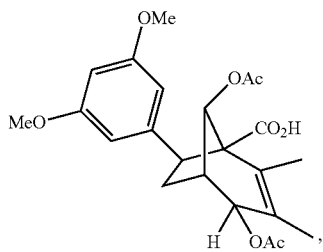

or an enantiomer, diastereomer, racemic mixture or a pharmaceutically acceptable salt thereof.

4. The compound of claim 1, having the formula:

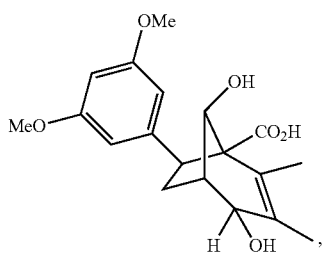

or an enantiomer, diastereomer, racemic mixture or a pharmaceutically acceptable salt thereof.

5. The compound of claim 1, having the formula:

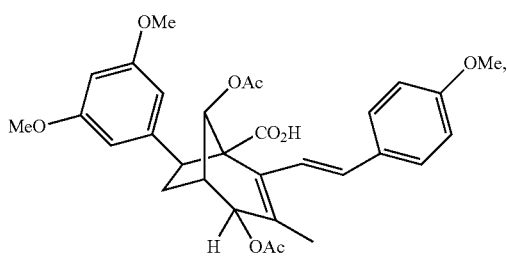 [SMILES: COc1ccc(/C=C/C2=C(C)C(OC(C)=O)C3CC(c4cc(OC)cc(OC)c4)C2(C(=O)O)C3OC(C)=O)cc1]

or an enantiomer, diastereomer, racemic mixture or a pharmaceutically acceptable salt thereof.

6. The compound of claim 1, having the formula:

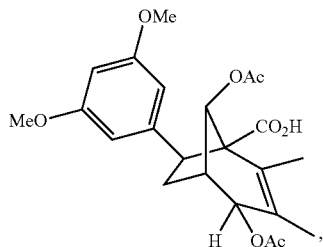 [SMILES: COc1cc(OC)cc(C2CC3C(OC(C)=O)C(C)=C(C)C2(C(=O)O)C3OC(C)=O)c1]

or an enantiomer, diastereomer, racemic mixture or a pharmaceutically acceptable salt thereof.

7. The compound of claim 1, having the formula:

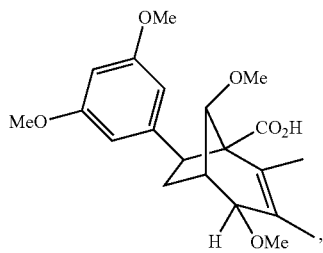 [SMILES: COc1cc(OC)cc(C2CC3C(OC)C(C)=C(C)C2(C(=O)O)C3OC)c1]

or an enantiomer, diastereomer, racemic mixture or a pharmaceutically acceptable salt thereof.

8. A composition comprising the compound of claim 1 and a pharmaceutically acceptable carrier.

9. The composition of claim 8, wherein the compound has the formula:

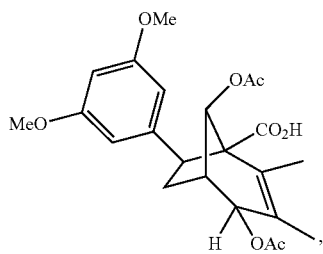 [SMILES: COc1cc(OC)cc(C2CC3C(OC(C)=O)C(C)=C(C)C2(C(=O)O)C3OC(C)=O)c1]

or an enantiomer, diastereomer, racemic mixture or a pharmaceutically acceptable salt thereof.

10. The composition of claim 8, wherein the compound has the formula:

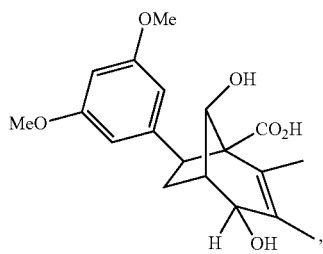 [SMILES: COc1cc(OC)cc(C2CC3C(O)C(C)=C(C)C2(C(=O)O)C3O)c1]

or an enantiomer, diastereomer, racemic mixture or a pharmaceutically acceptable salt thereof.

11. The composition of claim 8, wherein the compound has the formula:

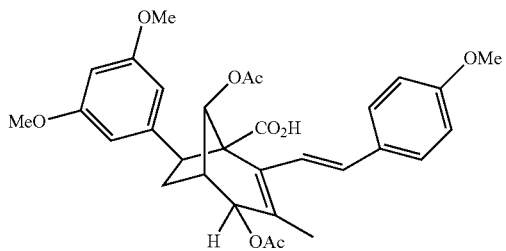 [SMILES: COc1ccc(/C=C/C2=C(C)C(OC(C)=O)C3CC(c4cc(OC)cc(OC)c4)C2(C(=O)O)C3OC(C)=O)cc1]

or an enantiomer, diastereomer, racemic mixture or a pharmaceutically acceptable salt thereof.

12. The composition of claim 8, wherein the compound has the formula:

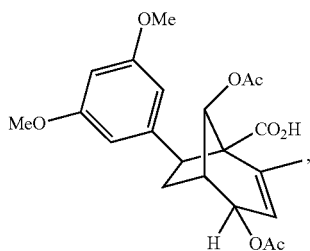 [SMILES: COc1cc(OC)cc(C2CC3C(OC)C=C(C)C2(C(=O)O)C3OC)c1]

or an enantiomer, diastereomer, racemic mixture or a pharmaceutically acceptable salt thereof.

13. The composition of claim 9, wherein the compound has the formula:

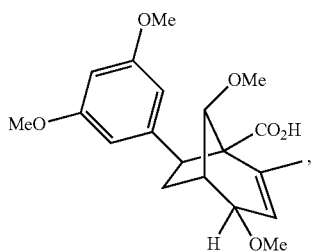

or an enantiomer, diastereomer, racemic mixture or a pharmaceutically acceptable salt thereof.

14. A method of reducing neurological damage due to cellular stress in an individual comprising administering to the individual during or after the cellular stress a compound according to claim 1 or a composition according to claim 8 in a therapeutically effective amount to restore synaptic function during or after the cellular stress, wherein the cellular stress is anoxia or oxidative stress.

15. The method of claim 14, wherein the cellular stress is caused by at least one selected from the group consisting of migraine, Alzheimer's disease, traumatic brain injury, heart attack and stroke.

16. The method of claim 14, wherein the cellular stress is acute oxidative stress.

17. The method of claim 14, wherein administering the compound or composition to the individual increases time until synaptic failure.

18. The method of claim 14, further comprising detecting a state or condition of cellular stress in the individual prior to administering to the individual during or after the cellular stress a compound according to claim 1 or a composition according to claim 8.

19. A compound of Formula 1:

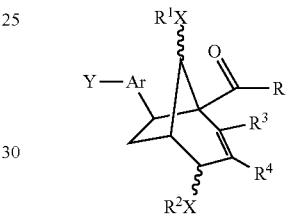

or an enantiomer, diastereomer, racemic mixture or a pharmaceutically acceptable salt or solvate thereof, wherein:

Ar is 5- or 6- membered heteroaryl;

Y is an ortho, meta, or para heteroaryl substituent selected from the group consisting of alkyl, alkyloxy, alkylamino, $NR^5R^6$, and halo;

X is O, S, or NH bonded to $R^1$ or $R^2$;

R is H, alkyl, heteroaryl, OH, alkyloxy, heteroaryloxy, $NH_2$, alkylamino, $NR^5R^6$, or heteroarylamino;

$R^1$ and $R^2$ are alkylcarbonyl, heteroarylcarbonyl, alkyl, or H, individually;

$R^3$ is heteroarylCH=CH, alkylCH=CH, or alkyl;

$R^4$ is H, alkyl, or heteroaryl; and $R^5$ and $R^6$ are alkyl, individually.

* * * * *